US009333650B2

(12) United States Patent
Bajo et al.

(10) Patent No.: US 9,333,650 B2
(45) Date of Patent: May 10, 2016

(54) METHOD AND SYSTEM FOR CONTACT DETECTION AND CONTACT LOCALIZATION ALONG CONTINUUM ROBOTS

(71) Applicant: Vanderbilt University, Nashville, TN (US)

(72) Inventors: Andrea Bajo, Hermitage, TN (US); Nabil Simaan, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 135 days.

(21) Appl. No.: 13/891,389

(22) Filed: May 10, 2013

(65) Prior Publication Data

US 2013/0300537 A1    Nov. 14, 2013

Related U.S. Application Data

(60) Provisional application No. 61/645,734, filed on May 11, 2012.

(51) Int. Cl.
*B25J 9/16*    (2006.01)
*A61B 19/00*    (2006.01)

(52) U.S. Cl.
CPC ............. *B25J 9/163* (2013.01); *A61B 19/2203* (2013.01); *A61B 2019/2219* (2013.01); *A61B 2019/2238* (2013.01); *A61B 2019/465* (2013.01)

(58) Field of Classification Search
CPC ................ B25J 9/163; A61B 19/2203; A61B 2019/465; A61B 2019/2238; A61B 2019/2219; A61B 2019/2211; A61B 19/2215; A61B 2019/2234; A61B 2019/2249; A61B 2019/2292; A61B 2019/2296

USPC ........................................... 340/8.1; 604/500
See application file for complete search history.

(56) References Cited

U.S. PATENT DOCUMENTS

| 4,744,264 | A | 5/1988 | Milenkovic |
| 4,802,461 | A | 2/1989 | Cho |
| 5,337,732 | A | 8/1994 | Grundfest et al. |
| 5,386,741 | A | 2/1995 | Rennex |
| 5,662,587 | A | 9/1997 | Grundfest et al. |
| 5,749,828 | A | 5/1998 | Solomon et al. |
| 6,309,346 | B1 | 10/2001 | Farhadi |

(Continued)

FOREIGN PATENT DOCUMENTS

| EP | 2335558 | 6/2011 |
| WO | 2005009482 | 2/2005 |

(Continued)

OTHER PUBLICATIONS

A. Bajo and N. Simaan, "Finding Lost Wrenches: Using Continuum Robots for Contact Detection and Estimation of Contact Location," 2010 IEEE International Conference on Robotics and Automation (May 3-8, 2010).

(Continued)

*Primary Examiner* — Jennifer Mehmood
*Assistant Examiner* — Yong Hang Jiang
(74) *Attorney, Agent, or Firm* — Michael Best & Friedrich LLP

(57) ABSTRACT

A robotic system and methods for manipulation of multi-segment continuum robots. The methods relate to contact detection and estimation of contact location along a multi-segment continuum robot.

18 Claims, 13 Drawing Sheets

(56) References Cited

U.S. PATENT DOCUMENTS

| | | | |
|---|---|---|---|
| 6,669,711 B1 | 12/2003 | Noda | |
| 6,817,974 B2 | 11/2004 | Cooper et al. | |
| 7,099,745 B2 | 8/2006 | Ebert | |
| 7,682,319 B2 | 3/2010 | Martin et al. | |
| 7,787,681 B2 | 8/2010 | Zhang et al. | |
| 7,822,249 B2 | 10/2010 | Garty et al. | |
| 7,837,615 B2 | 11/2010 | Le et al. | |
| 8,116,886 B2 | 2/2012 | Simaan et al. | |
| 8,365,633 B2 | 2/2013 | Simaan et al. | |
| 8,864,757 B2 * | 10/2014 | Klimovitch | A61B 5/042 600/437 |
| 2004/0116906 A1 | 6/2004 | Lipow | |
| 2005/0054900 A1 | 3/2005 | Mawn et al. | |
| 2005/0059960 A1 | 3/2005 | Simaan et al. | |
| 2006/0036182 A1 | 2/2006 | Daniels et al. | |
| 2006/0058861 A1 | 3/2006 | Gibson et al. | |
| 2006/0156851 A1 | 7/2006 | Jacobsen et al. | |
| 2007/0225787 A1 | 9/2007 | Simaan et al. | |
| 2008/0114492 A1 | 5/2008 | Miegel et al. | |
| 2008/0179301 A1 | 7/2008 | Garty et al. | |
| 2008/0181473 A1 | 7/2008 | Garty et al. | |
| 2008/0243063 A1 | 10/2008 | Camarillo | |
| 2008/0245173 A1 | 10/2008 | Schwerin et al. | |
| 2008/0302200 A1 | 12/2008 | Tobey | |
| 2009/0054222 A1 | 2/2009 | Zhang et al. | |
| 2009/0076476 A1 * | 3/2009 | Barbagli et al. | 604/500 |
| 2009/0076521 A1 | 3/2009 | Hansen | |
| 2009/0088774 A1 | 4/2009 | Swarup et al. | |
| 2009/0171151 A1 | 7/2009 | Choset et al. | |
| 2009/0216083 A1 | 8/2009 | Durant et al. | |
| 2009/0275818 A1 | 11/2009 | Rau et al. | |
| 2009/0275857 A1 | 11/2009 | Cabiri et al. | |
| 2010/0010504 A1 | 1/2010 | Simaan et al. | |
| 2010/0011900 A1 | 1/2010 | Burbank | |
| 2010/0030377 A1 | 2/2010 | Unsworth | |
| 2010/0069719 A1 | 3/2010 | Wehrheim | |
| 2010/0076269 A1 | 3/2010 | Makower et al. | |
| 2010/0099951 A1 | 4/2010 | Laby et al. | |
| 2010/0125165 A1 | 5/2010 | Torii et al. | |
| 2010/0152899 A1 | 6/2010 | Chang et al. | |
| 2010/0256558 A1 * | 10/2010 | Olson et al. | 604/95.01 |
| 2010/0331858 A1 | 12/2010 | Simaan et al. | |
| 2011/0015649 A1 * | 1/2011 | Anvari et al. | 606/130 |
| 2011/0066160 A1 | 3/2011 | Simaan et al. | |
| 2011/0125165 A1 | 5/2011 | Simaan et al. | |
| 2011/0184241 A1 | 7/2011 | Zubiagte et al. | |
| 2011/0213346 A1 | 9/2011 | Morley et al. | |
| 2011/0230894 A1 | 9/2011 | Simaan et al. | |
| 2011/0306929 A1 * | 12/2011 | Levesque et al. | 604/150 |
| 2011/0313243 A1 | 12/2011 | Zubiate et al. | |
| 2011/0319910 A1 | 12/2011 | Roelle et al. | |
| 2012/0109274 A1 | 5/2012 | Simaan et al. | |
| 2013/0090763 A1 * | 4/2013 | Simaan et al. | 700/258 |
| 2013/0131868 A1 | 5/2013 | Rucker et al. | |
| 2013/0197539 A1 | 8/2013 | Simaan et al. | |
| 2013/0289581 A1 | 10/2013 | Yeung et al. | |
| 2013/0338433 A1 * | 12/2013 | Goldman | A61B 1/0052 600/102 |
| 2014/0058406 A1 | 2/2014 | Tsekos | |
| 2014/0330432 A1 | 11/2014 | Simaan et al. | |
| 2015/0073434 A1 | 3/2015 | Simaan et al. | |

FOREIGN PATENT DOCUMENTS

| | | |
|---|---|---|
| WO | 2005112834 | 12/2005 |
| WO | 2008036304 | 3/2008 |
| WO | 2009094670 | 7/2009 |
| WO | 2009097461 | 8/2009 |
| WO | 2009097539 | 8/2009 |
| WO | 2009124287 | 10/2009 |
| WO | 2009140688 | 11/2009 |
| WO | 2010042611 | 4/2010 |
| WO | 2011063511 | 6/2011 |
| WO | 2012015816 | 2/2012 |
| WO | 2012049623 | 4/2012 |
| WO | 2013158974 | 10/2013 |
| WO | 2013158978 | 10/2013 |
| WO | 2013158983 | 10/2013 |
| WO | 2013166293 | 11/2013 |

OTHER PUBLICATIONS

Bajo, A., Goldman, R. E., Wang, L., Fowler, D. & Simaan, N (2012). Integration and Preliminary Evaluation of an Insertable Robotic Effectors Platform for Single Port Access Surgery. In International Conference on Robotics and Automation (ICRA'2012), pp. 3381-3387.

Bajo, A., Pickens, R. B., Herrell, D. S. & Simaan, N (2012). A Pilot Ex-Vivo Evaluation of a Telerobotic System for Transurethral Intervention and Surveillance. In Hamlyn Symposium on Medical Robotics.

Bajo, A., Pickens, R. B., Herrell, D. S. & Simaan, N (2013). Constrained Motion Control of Multisegment Continuum Robots for Transurethral Bladder Resection and Surveillance. In Accepted for publication in IEEE International Conference on Robotics and Automation (ICRA'2013).

A. Kapoor, K. Xu, W. Wei, N. Simaan, and R. Taylor, "Telemanipulation of Snake-Like Robots for Minimally Invasive Surgery of the Upper Airway," in MICCAI 2006 workshop on medical robotics, 2006.

A. Kapoor, N. Simaan, and P. Kazanzides, "A System for Speed and Torque Control of DC Motors with Application to Small Snake Robots," 2004.

A. Kapoor, N. Simaan, and R. Taylor, "Suturing in Confined Spaces: Constrained Motion Control of a Hybrid 8-DoF Robot", in IEEE Conference on Advanced Robotics, 2005, pp. 452-459.

Abbott, J., Marayong, P., and Okamura, A. M. Haptic virtual fixtures for robot-assisted manipulation. Robotics Research 28, Aug. 2007, 49-64.

Alexander T. Hillel, Ankur Kapoor, Nabil Simaan, Russell H. Taylor and Paul Flint, "Applications of Robotics for Laryngeal Surgery," Otolaryngologic Clinics of North America, Nasir Bhatti & Ralph P. Tufano Eds., vol. 41, Issue 4, pp. 781-791, doi:0.1016/j.otc.2008.01. 021, Aug. 2008.

Chen, Y., Zhang, J., Wang, H., Garty, G., Xu, Y., Lyulko, O., Turner, H., Randers-Pehrson, G., Simaan, N., Yao, L., Brenner, D., "Development of a Robotically-based Automated Biodosimetry Tool for Highthroughput Radiological Triage," accepted in International Journal of Biomechatronics and Biomedical Robotics (IJBBR), vol. 1, No. 2 pp. 115-125, 2010.

Debus, T., Dupont, P., and Howe, R. Contact State Estimation using Multiple Model Estimation and Hidden Markov Models. 2The International Journal of Robotics Research 23, 4-5 (2004), 399-413.

Ding, J., Xu, K., Goldman, R. E., Allen, P. K., Fowler, D. L., and Simaan, N. "Design, Simulation and Evaluation of Kinematic Alternatives for Insertable Robotic Effectors Platforms in Single Port Access Surgery," In 2010 IEEE International Conference on Robotics and Automation (Anchorage, AK, 2010), pp. 1053-1058.

Godage, Isuru S. et al., "Shape Function-Based Kinematics and Dynamics for Variable Length Continuum Robotic Arms," 2011 IEEE International Conference on Robotics and Automation (May 9-13, 2011).

R. E. Goldman, A. Bajo, and N. Simaan, "Compliant Motion Control for Continuum Robots with Intrinsic Actuation Sensing," in IEEE International Conference on Robotics and Automation, 2011, pp. 1126-1132.

Gravagne, Ian A. and Ian D. Walker, "Manipulability, Force, and Compliance Analysis for Planar Continuum Manipulators," IEEE Transactions on Robotics and Automation, vol. 18, No. 3 (Jun. 2002).

Gravagne, Ian A. et al, "Good Vibrations: A Vibration Damping Setpoint Controller for Continuum Robots," Proceedings of the 2001 IEEE International Conference on Robotics & Automation (May 21-26, 2001).

Hamid, S. A. & Simaan, N (2009). Design and Synthesis of Wire-Actuated Universal-Joint Wrists for Surgical Applications. In 2009 IEEE International Conference on Robotics and Automation, pp. 1807-1831. Kobe, Japan.

(56) References Cited

OTHER PUBLICATIONS

Hannan, M. W., and Walker, I. D. Kinematics and the Implementation of an Elephant's Trunk Manipulator and Other Continuum Style Robots. Journal of Robotic Systems 20, 2 (2003), 45-63.
Hayward, Vincent, "Fast Collision Detection Scheme by Recursive Decomposition of A Manipulator Workspace," Proceedings IEEE International Conference on Robotics and Automation, vol. 3 (1986).
Hogan, N. Impedance Control: An Approach to Manipulation: Part ITheory. Journal of Dynamic Systems, Measurement, and Control 107, 1 (1985), 1.
International Search Report and Written Opinion for PCT Application No. PCT/US2013/021167 dated Mar. 22, 2013.
International Search Report and Written Opinion for PCT Application No. PCT/US2013/037336 dated Jul. 25, 2013.
International Search Report and Written Opinion for PCT Application No. PCT/US2013/037346 dated Aug. 27, 2013.
International Search Report and Written Opinion for PCT Application No. PCT/US2013/037353 dated Aug. 19, 2013.
International Search Report and Written Opinion for PCT Application No. PCT/US2013/039280 dated Aug. 20, 2013.
J. Ding, K. Xu, R. Goldman, P. Allen, D. Fowler, and N. Simaan, "Design, Simulation and Evaluation of Kinematic Alternatives for Insertable Robotic Effectors Platforms in Single Port Access Surgery." pp. 1053-1058, 2010.
J. J. Abbott and A. M. Okamura, "Stable Forbidden-Region Virtual Fixtures for Bilateral Telemanipulation," vol. 128, No. 1, pp. 53-64, 2006.
J. Zhang, S. Bhattacharyya, and N. Simaan, "Model and Parameter Identification of Friction During Robotic Insertion of Cochlear-Implant Electrode Arrays," in IEEE International Conference on Robotics and Automation, 2009, pp. 3859-3864.
Jones, Bryan A., "Kinematics for Multisection Continuum Robots," IEEE Transactions on Robotics, vol. 22, No. 1 (Feb. 2006).
K. Xu and N. Simaan, "Actuation Compensation for Flexible Surgical Snake-like Robots with Redundant Remote Actuation," in IEEE International Conference on Robotics and Automation, 2006, pp. 4148-4154.
K. Xu and N. Simaan, "Analytic Formulation for Kinematics, Statics and Shape Restoration of Multibackbone Continuum Robots via Elliptic Integrals," ASME Journal of Mechanisms and Robotics (JMR), vol. 2, pp. 11006-11013, 2010.
K. Xu, R. Goldman, J. Ding, P. Allen, D. Fowler, and N. Simaan, "System Design of an Insertable Robotic Effector Platform for Single Port Access (SPA) Surgery," in IEEE/RSJ International Conference on Intelligent Robots and Systems, 2009, pp. 5546-5552.
K. Xu and N. Simaan, "An Investigation of the Intrinsic Force Sensing Capabilities of Continuum Robots," IEEE Transactions on Robotics (TRO), vol. 23, No. 3 (Jun. 2008).
Mahvash, Mohsen and Pierre E. Dupont, "Stiffness Control of a Continuum Manipulator in Contact with a Soft Environment," The 2010 IEEE/RSJ International Conference on Intelligent Robots and Systems (Oct. 18-22, 2010).
Mahvash, Mohsen and Pierre E. Dupont, "Stiffness Control of Surgical Continuum Manipulators," IEEE Transactions on Robotics, vol. 27, No. 2 (Apr. 2011).
N. Simaan, A. Bajo, A. Reiter, L. Wang, P. Allen, and D. Fowler, "Lessons learned using the insertable robotic effector platform (IREP) for single port access surgery," Journal of Robotic Surgery, Apr. 2013.
N. Simaan, R. Taylor, and P. Flint, "A Dexterous System for Laryngeal Surgery—Multi-Backbone Bending Snake-like Slaves for Teleoperated Dexterous Surgical Tool Manipulation." pp. 351-357, 2004.
N. Simaan, "Snake-Like Units Using Flexible Backbones and Actuation Redundancy for Enhanced Miniaturization," In 2005 IEEE International Conference on Robotics and Automation (Barcelona, Spain, 2005), IEEE, pp. 3023-3028.

N. Simaan, Russell H. Taylor, Paul Flint, "High Dexterity Snake-like Robotic Slaves for Minimally Invasive Telesurgery of the Upper Airway," MICCAI 2004 (7th International Conference on Medical Image Computing and Computer-Assisted Intervention), pp. 17-24, vol. 2, Saint Malo, France, Sep. 26-30, 2004.
Simaan, N., Glozman, D. & Shoham, M (1998). Design Considerations of New Six Degrees-of-Freedom Parallel Robots. In IEEE International Confernce on Robotics and Automation (ICRA'1998), pp. 1327-1333.
Simaan, N. (1999). Analysis and Synthesis of Parallel Robots for Medical Applications. Master Thesis, Technion-Israel Institute of Technology, Haifa, Israel.
N. Simaan, Task-Based Design and Synthesis of Variable Geometry Parallel Robots (2002). Phd Thesis, Technion-Israel Institute of Technology, Haifa, Israel.
Pickens, R. B., Bajo, A., Simaan, N. & Herrell, S. D (2012). Preliminary Testing of a Transurethral Dexterous Robotic System for Bladder Resecton. In 27th EUS Annual Meeting, pp. 65, Atlanta, GA.
Pile, J., Cheung, M.-Y., Zhang, J. & Simaan, N (2011). Algorithms and Design Considerations for Robot Assisted Insertion of Perimodiolar Electrode Arrays. In 2011 IEEE International Conference on Robotics and Automation. Shanghai, China.
R. Taylor et al., "Steady-hand robotic system for microsurgical augmentation," International Journal of Robotics Research, vol. 18, No. 12, pp. 1201-1210, 1999.
Reiter, A., Bajo, A., Iliopoulos, K., Simaan, N., and Allen, P. K. Learning-Based Configuration Estimation of a Multi-Segment Continuum Robot. In The Fourth IEEE RAS/EMBS International Conference on Biomedical Robotics and Biomechatronics (Roma, Italy, 2012), p. accepted.
Reiter, A., Goldman, R. E., Bajo, A., Iliopoulos, K., Simaan, N., and Allen, P. K. A Learning Algorithm for Visual Pose Estimation of Continuum Robots. In 2011 IEEE/RSJ International Conference on Intelligent Robots and Systems (San Francisco, CA, USA, 2011), pp. 2390-2396.
Rivera-Serrano, C. M., Johnson, P., Zubiate, B., Kuenzler, R., Choset, H., Zenati, M., Tully, S., and Duvvuri, U. A transoral highly flexible robot: Novel technology and application. The Laryngoscope 122, May 5, 2012, 1067-1071.
Sen, T. H., Deshmukh, N., Roger E, .. G., Kazanzides, P., Taylor, R. H., Boctor, E. et al (2012). Enabling technologies for natural orifice transluminal endoscopic surgery (N.O.T.E.S) using robotically guided elasticity imaging. In Proceeding of SPIE Medical Imaging 2012, pp. 83161Y1-83161Y8.
Tully, S., Bajo, A., Kantor, G., Choset, H., and Simaan, N. Constrained Filtering with Contact Detection Data for the Localization and Registration of Continuum Robots in Flexible Environments. In 2012 IEEE International Conference on Robotics and Automation (St. Paul, MI USA, 2012).
W. Wei, K. Xu, and N. Simaan, "A compact Two-armed Slave Manipulator for Minimally Invasive Surgery of the Throat," in IEEE RAS/EMBS International Conference on Biomedical Robotics and Biomechatronics, 2006, pp. 769-774.
Wei, W., Goldman, R. E., Simaan, N., Fine, H. & Chang, S (2007). Design and Theoretical Evaluation of Micro-Surgical Manipulators for Orbital Manipulation and Intraocular Dexterity. In 2007 IEEE International Conference on Robotics and Automation, pp. 3389-3395. Roma, Italy.
Wei, W., and Simaan, N. Modeling, Force Sensing, and Control of Flexible Cannulas for Microstent Delivery. Journal of Dynamic Systems, Measurement, and Control 134, 4 (2012), 041004.
Wei, W., Popplewell, C., Fine, H., Chang, S., Simaan, N., "Enabling Technology for Micro-Vascular Stenting in Ophthalmic Surgery," ASME Journal of Medical Devices (JMED), vol. 4, Issue 1, 014503 (6 pages) doi:10.1115/1.4001193, 2010.
U.S. Office action for U.S. Appl. No. 14/271,418 dated May 20, 2015.

* cited by examiner

TABLE III
CONTACT ESTIMATION ALONG THE FIRST SEGMENT. UNITS OF MM

| $d_i$ | T | $d_0$ | $d_1$ | $d_2$ | $d_3$ | $d_4$ | $d_5$ | $d_6$ | $d_7$ |
|---|---|---|---|---|---|---|---|---|---|
| 3 | 1 | 9.2 | 6.0 |  | 3.6 | 6.3 | 9.6 | 13.0 | 16.5 |
|   | 2 | 7.7 | 4.7 |  | 4.7 | 7.8 | 11.1 | 14.6 | 18.0 |
|   | 3 | 9.8 | 6.4 | 3.5 |  | 5.4 | 8.7 | 12.2 | 15.7 |
|   | 4 | 9.8 | 6.6 | 4.1 |  | 6.2 | 9.4 | 12.7 | 16.1 |
|   | 5 | 10.4 | 7.1 | 4.2 |  | 5.3 | 8.4 | 11.8 | 15.2 |
| 4 | 1 | 11.7 | 8.4 | 5.6 |  | 5.2 | 7.9 | 11.1 | 14.5 |
|   | 2 | 11.9 | 8.7 | 6.0 |  | 5.4 | 8.0 | 11.0 | 14.4 |
|   | 3 | 11.7 | 8.6 | 6.0 |  | 5.7 | 8.3 | 11.4 | 14.7 |
|   | 4 | 11.7 | 8.5 | 5.7 |  | 5.2 | 7.9 | 11.1 | 14.4 |
|   | 5 | 11.3 | 8.1 | 5.2 |  | 5.1 | 7.9 | 11.2 | 14.6 |
| 5 | 1 | 14.6 | 11.3 | 8.2 | 5.4 |  | 5.0 | 7.7 | 10.8 |
|   | 2 | 15.0 | 11.6 | 8.3 | 5.3 |  | 4.0 | 6.9 | 10.1 |
|   | 3 | 15.6 | 12.4 | 9.2 | 6.3 |  | 4.7 | 7.0 | 10.0 |
|   | 4 | 16.2 | 12.9 | 9.7 | 7.1 |  | 5.4 | 7.4 | 10.2 |
|   | 5 | 15.6 | 12.5 | 9.7 | 7.5 |  | 7.1 | 9.1 | 11.8 |

FIG. 14

TABLE IV
CONTACT ESTIMATION ALONG THE SECOND SEGMENT. UNITS OF MM

| $d_i$ | T | $d_0$ | $d_1$ | $d_2$ | $d_3$ | $d_4$ | $d_5$ | $d_6$ | $d_7$ |
|---|---|---|---|---|---|---|---|---|---|
| 2 | 1 | 7.0 |  | 6.3 | 8.4 | 11.0 | 14.1 | 17.2 | 20.4 |
|   | 2 | 5.9 |  | 5.7 | 8.1 | 11.1 | 14.3 | 17.6 | 20.9 |
|   | 3 | 6.3 |  | 5.0 | 7.4 | 10.4 | 13.7 | 17.0 | 20.4 |
|   | 4 | 7.8 |  | 6.7 | 8.4 | 10.9 | 13.8 | 16.9 | 20.0 |
|   | 5 | 6.1 |  | 4.1 | 6.7 | 9.8 | 13.1 | 16.5 | 19.9 |
| 3 | 1 | 11.8 | 10.4 |  | 10.5 | 12.0 | 14.0 | 16.5 | 19.3 |
|   | 2 | 13.1 | 11.2 | 10.0 |  | 10.6 | 12.3 | 14.6 | 17.2 |
|   | 3 | 13.2 | 11.3 | 10.1 |  | 10.7 | 12.3 | 14.7 | 17.3 |
|   | 4 | 13.0 | 11.0 | 9.6 |  | 10.0 | 11.7 | 14.1 | 16.8 |
|   | 5 | 13.1 | 11.1 | 9.8 |  | 10.4 | 12.1 | 14.4 | 17.1 |
| 4 | 1 | 18.1 | 15.8 | 13.8 | 12.4 |  | 11.9 | 13.0 | 14.8 |
|   | 2 | 17.9 | 15.4 | 13.3 | 11.8 |  | 11.1 | 12.2 | 14.0 |
|   | 3 | 17.6 | 15.2 | 13.2 | 11.7 |  | 11.4 | 12.6 | 14.4 |
|   | 4 | 18.7 | 16.3 | 14.2 | 12.6 |  |  | 12.4 | 14.0 |
|   | 5 | 17.8 | 15.2 | 13.2 | 11.6 |  | 11.1 | 12.2 | 14.1 |
| 5 | 1 | 20.3 | 17.1 | 13.9 | 10.7 | 7.8 | 5.6 |  | 6.7 |
|   | 2 | 22.2 | 19.2 | 16.4 | 13.7 | 11.4 | 9.7 |  | 9.5 |
|   | 3 | 21.6 | 18.7 | 16.0 | 13.5 | 11.4 | 10.0 |  | 10.4 |
|   | 4 | 22.0 | 19.0 | 16.3 | 13.7 | 11.5 | 10.0 |  | 10.1 |
|   | 5 | 21.0 | 18.1 | 15.3 | 12.7 | 10.5 | 9.1 |  | 9.9 |

FIG. 15

TABLE V
CONTACT ESTIMATION ALONG THE THIRD SEGMENT. UNITS OF MM

| $d_i$ | T | $d_0$ | $d_1$ | $d_2$ | $d_3$ | $d_4$ | $d_5$ | $d_6$ | $d_7$ |
|---|---|---|---|---|---|---|---|---|---|
| 2 | 1 | 7.6 | 5.1 | ■ | 4.8 | 7.3 | 10.1 | 13.2 | 16.2 |
|   | 2 | 8.7 | 7.3 | ■ | 8.1 | 10.0 | 12.5 | 15.2 | 18.0 |
|   | 3 | 5.1 | ■ | 4.2 | 6.7 | 9.7 | 12.7 | 15.8 | 18.9 |
|   | 4 | 5.3 | ■ | 5.5 | 7.9 | 10.7 | 13.6 | 16.6 | 19.7 |
|   | 5 | 7.2 | ■ | 7.4 | 9.3 | 11.7 | 14.4 | 17.2 | 20.1 |
| 3 | 1 | 12.2 | 9.4 | 6.9 | 5.1 | ■ | 6.6 | 9.0 | 11.8 |
|   | 2 | 15.7 | 13.2 | 10.9 | 9.0 | ■ | 8.1 | 9.2 | 11.1 |
|   | 3 | 14.8 | 12.6 | 10.7 | 9.4 | ■ | 9.6 | 11.0 | 13.0 |
|   | 4 | 15.3 | 12.4 | 9.6 | 7.0 | 5.2 | ■ | 6.5 | 8.9 |
|   | 5 | 15.1 | 12.6 | 9.3 | 6.4 | ■ | 6.2 | 7.1 | 11.2 |
| 4 | 1 | 12.0 | 10.2 | 9.1 | ■ | 9.8 | 11.4 | 13.6 | 16.0 |
|   | 2 | 14.5 | 11.8 | 9.3 | 7.2 | ■ | 6.3 | 7.9 | 10.3 |
|   | 3 | 12.6 | 10.7 | 9.5 | ■ | 9.5 | 10.9 | 12.9 | 15.2 |
|   | 4 | 13.6 | 10.9 | 8.6 | 6.9 | ■ | 7.1 | 9.0 | 11.4 |
|   | 5 | 11.6 | 9.6 | 7.6 | ■ | 7.3 | 8.9 | 11.1 | 13.6 |

FIG. 16

METHOD AND SYSTEM FOR CONTACT DETECTION AND CONTACT LOCALIZATION ALONG CONTINUUM ROBOTS

RELATED APPLICATIONS

This application claims priority to U.S. Provisional Patent Application No. 61/645,734, filed on May 11, 2013, the entire contents of which are incorporated herein by reference.

STATEMENT REGARDING FEDERALLY SPONSORED RESEARCH OR DEVELOPMENT

This invention was made with government support under grant IIS-1063750 awarded by the National Science Foundation. The government has certain rights in the invention.

FIELD OF THE INVENTION

The present invention relates to methods for manipulation of continuum segment robots. More specifically, the present invention relates to methods for contact detection and estimation of contact location along continuum segment robots. Though the algorithms are described for multi-segment continuum robots they equally apply to other configurations of continuum robots including wire-actuated catheters and concentric tube robots.

BACKGROUND OF THE INVENTION

Current robotic systems are incapable of fully characterizing their interaction with the environment. Full characterization of the interaction means: discerning collisions, localizing contact constraints, and estimating interaction forces. Although there are mature algorithms for compliant hybrid motion/force control, there exists no unified framework for the impact and post-impact phases. These algorithms require a priori knowledge of the environmental constraint geometry via formulation of natural and artificial constraints or motion and constraint screws. Previous works on rigid-link robots do not apply directly to continuum manipulators and do not provide a unified method for both collision detection and estimation of contact location without a priori knowledge of the environmental constraints and additional sensory devices such as robotic skins.

Previous works individually focused on collision detection, and estimation of constraint locations. For example, generalized momentum of serial robots was used to identify contact incidence and the link at which contact occurs. Additionally, a least-squares method using an estimate of contact location from tactile sensors and joint torque measurements to estimate the magnitude and the location of contact force was presented. Further, two different probabilistic approaches for contact estimation were proposed. Still other researchers have tried to overcome the limitations of rigid-link robots by developing sensitive robotic skins.

Continuum robots are continuously bending, infinite-degree-of-freedom elastic structures that offer an opportunity to overcome the limitations of rigid-link robots. This opportunity stems from the ability of continuum robots to change their shape when interacting with the environment.

The motivation behind investigation into methods for robot manipulation originates in the field of medical robotics. New surgical paradigms such as Natural Orifice Transluminal Endoscopic Surgery (NOTES) demand deeper anatomical reach along increasingly tortuous paths. Medical robots need to be intelligent to autonomously prevent inadvertent trauma to surrounding anatomy while accomplishing surgical tasks beyond the capabilities of conventional robotic platforms for Minimally Invasive Surgery (MIS) in order to meet the challenges of NOTES. Further, robots need to support automated or semi-automated insertion into the anatomy, regulate their contact forces along the whole structure, and use their multi-point interactions to enhance end-effector precision. Up until now, several researchers have relied on passive compliance of continuum robots and wire-actuated articulated robots. However, reliance on passive compliance of surgical robots comes with a price of performance degradation such as payload carrying capability and position accuracy.

SUMMARY OF THE INVENTION

Some embodiments of this invention provide a general framework for collision detection and contact location estimation along multi-segment continuum robots. Some embodiments also actively enhance safety of interaction by providing continuum robots with the ability to act as sensors as well as surgical intervention platforms.

The general framework for collision detection and contact estimation for an n-segment continuum robot provide by embodiments of this invention relies only on the relative motion of each segment with respect to its own base. By working in local frames, the methods' scalability is maximized. A Screw Motion Deviation (SMD) is proposed based on the nominal forward kinematics of the robot and exteroceptive sensory information. Online calculation of this deviation for each segment enables single- and multi-collision detection at multiple segments. Estimation of contact location is carried out by using a constrained kinematics model that describes the constrained motion of the continuum robot. Thus, the invention demonstrates the ability to estimate the location of contacts and detect collisions at any point along the robotic structure, multiple collisions acting at different segments, and total arm constraint.

The implementation of these methods is relevant in several ways. First, these methods are applicable to prevent damage to dual-arm robots in instances where inadvertent contact between arms occurs. Further, these methods are appropriate for applications that use contact detection to constrain the kinematics of arms to prevent trauma to bracing anatomy. For example, an implementation of these methods is a continuum robot intended to reach through a trocar or a resectoscope tube and contact the tip of the tube and still enable telemanipulation of remaining degrees of freedom. Additionally, implementations of these methods are compatible with applications where contact with surrounding geometry is used as a safety feature. Finally, unguided blind exploration of geometry, registration of the geometry with respect to the robots, and use with other exploratory manipulation methods for exploration of anatomical constraints on surgical tools are all potential applications of these methods.

In one embodiment, the invention provides a method for collision detection along a continuum robot including inserting a portion of the continuum robot having a plurality of independent segments into a cavity. The method further includes detecting contact between the robot and the cavity, and determining in which segment of the robot the contact occurred.

In another embodiment the invention provides a method for generating a constraint including inserting a continuum robot having a plurality of individual segments into a cavity, detecting contact between the robot and the cavity, and detecting in which segment of the robot the contact occurred.

The constraints are generated based on the contact data and the segment data. Once the robot is removed from the cavity, a tool is inserted into the cavity based on the identified constraints.

Other aspects of the invention will become apparent by consideration of the detailed description and accompanying drawings.

BRIEF DESCRIPTION OF THE DRAWINGS

FIGS. 14-16 report the results of contact estimation along the first, second and third segments, respectively.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1A:
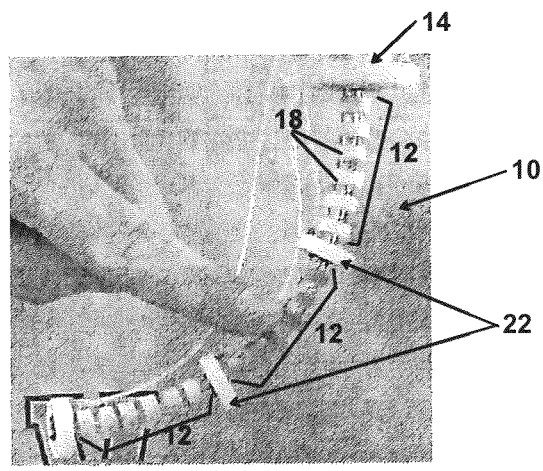
FIGS. 1a-1c illustrate a few scenarios of a multi-segment continuum robot in contact with a constraint.
Figure 1B:
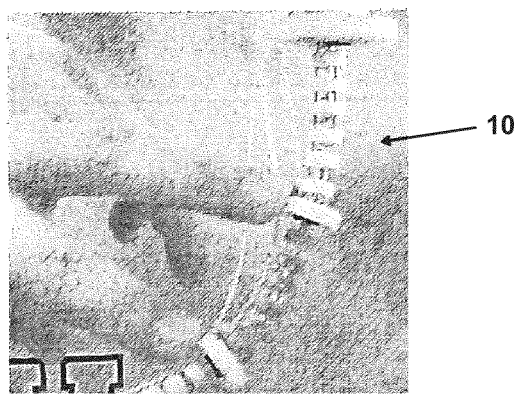
Figure 1C:
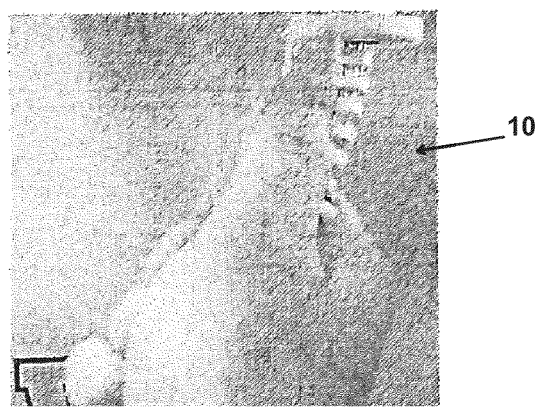

The following methods are relevant for multi-segment continuum robots 10 that bend in a known, repeatable shape. Examples of such multi-segment continuum robots are active catheters, tentacle/trunk robots, and multi-backbone continuum robots. With respect to FIGS. 1a-c and 2, these robots are composed of multiple independently actuated flexible segments where each segment bends in a circular shape. Each continuum segment (CS) 12 is composed of a base disk (BD) 14, several spacer disks (SD) 18, an end disk (ED) 22, and wires or backbones 26 depending on the particular actuation system. In the case of multi-backbone continuum robots, the primary backbone 30 is centrally located in each SD. A plurality of m secondary backbones 26 are evenly distributed around the central backbone 30 with division angle $\beta=2\pi/m$. The secondary backbones 26 are only attached to the ED 22 and they are used to bend the CS 12 using push-pull actuation. An example of a multi-segment continuum robot 10 where each segment bends in a circular shape is shown in FIGS. 1a-c.

Figure 2:
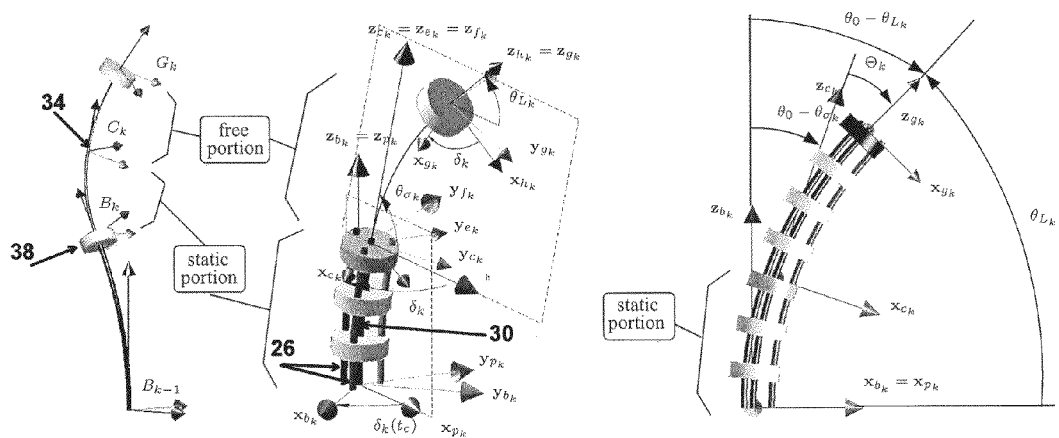
FIG. 2 illustrates the behavior of a multi-segment continuum robot when constrained.

Further, with reference to FIG. 2, the index of secondary backbones is represented by i, where i=1,2,m. The number of continuum segments is represented by n. The index of the robot's segments is indicated by k, where k=1, ..., n. Additional nomenclature relates $s_k$, $L_k$, and $\sigma_k$ to the arc-length parameter of the primary backbone of segment k, the nominal length of the primary backbone of segment k, and the arc-length specifying the contact location along the primary backbone, respectively. Additionally, r represents the radius of the pitch circle on which the secondary backbones are equally distributed with division angle $\beta$ around the primary backbone. Finally, the commanded right-handed rotation angle from $x_{P_k}$ about $z_{b_k}$ to a line pointing from the center of the base and passing through the primary backbone of the $i^{th}$ secondary backbone of segment k at is represented by $\delta_k$.

Contact detection and contact localization is determined as a result of a combination of kinematic theory and screw theory. Immediately after a constraint is applied (i.e., a collision), constrained kinematics is applied to characterize the behavior of a robot 10 having k continuum segments 12. Specifically, constrained kinematics describes a CS, in point-contact at an arbitrary arc-length location $\sigma_k$, where $\sigma_k \in [0, L_k]$. The following relationships are based on the fact that each CS bends in a circular shape and the gravitational forces are negligible for small continuum robots. Further, a distally constrained segment will affect the motion of all preceding segments, but a proximal constrained segment will not affect the motion of subsequent distal segments. Finally, the constrained portion of a constrained segment remains fixed while the free portion bends in the same fashion as the shorter segment. The kinematics nomenclature is illustrated in FIG. 2.

Constrained direct kinematics is used to determine a position $P_{Ck}^{bk}$, orientation $R_{Ck}^{bk}$, and bending angle $\theta_k(s_k)$. Therefore, immediately after the CS collides with a cavity a position $P_{Ck}^{bk}$, orientation $R_{Ck}^{bk}$, and bending angle $\theta_{\sigma_k}$ of a contact frame $\{C_k\}$ 34 with respect to a local base frame $\{B_k\}$ 38. The position $P_{Ck}^{bk}$ and orientation $R_{Ck}^{bk}$ are given by:

$$p_{c_k}^{b_k} = R_{P_k}^{b_k} \frac{L_k}{\theta_0 - \theta_{L_k}(t_c)} \begin{bmatrix} 1 - \sin\theta_{\sigma_k} \\ 0 \\ \cos\theta_{\sigma_k} \end{bmatrix} \quad (1)$$

$$R_{c_k}^{b_k} = R_{P_k}^{b_k} R_{e_k}^{P_k} R_{c_k}^{e_k}, \quad (2)$$

where $R_{Pk}^{bk} = e^{-\delta_k(t_c)e_{3x}}$, $$R_{c_k}^{P_k} = e^{(\theta_0 - \theta_{\sigma_k})e_{2x}},$$

and $R_k^{Ck} = e^{\delta_k(t_c)e_{3x}}$ denote the exponential forms for these rotations, $e_2$ and $e_3$ are the canonical unit vectors along the y and z axes, where $\theta_{L_k}(t_c)$ is the bending angle at the time of contact $t_c$ and more specifically, the commanded bending angle of the unconstrained segment. Further, the angle when $\delta_k$ is equal to zero is represented by $\theta_0$. The value of $\theta_{\sigma_k}$ is computed by:

$$\theta_{\sigma_k} = \theta_0 - \frac{\sigma_k}{L_k}(\theta_0 - \theta_{L_k}(t_c)) \qquad (3)$$

Using (1) and (2) position $P_{g_k}^{b_k}$ and orientation $R_{g_k}^{b_k}$ of the ED of the constrained segment is given by:

$$p_{g_k}^{b_k} = p_{c_k}^{b_k} + R_{c_k}^{b_k} R_{f_k}^{c_k} \frac{L_k - \sigma_k}{\Theta_k} \begin{bmatrix} 1 - \cos\Theta_k \\ 0 \\ \sin\Theta_k \end{bmatrix} \qquad (4)$$

$$R_{g_k}^{b_k} = R_{c_k}^{b_k} R_{f_k}^{c_k} R_{h_k}^{f_k} R_{g_k}^{h_k} \qquad (5)$$

where $\theta_k = \theta_{\sigma_k} - \theta_{L_k}$ and the rotation matrices in (5) are defined similarly as in (2) with rotation angles $\delta_k(t)$, and $\theta_k$ respectively.

When the CS is not in contact, i.e., $\theta_k = 0$, (3) reads $\theta_{\sigma_k} = \theta_{L_k}$, (1) and (2) reduce to zero, and reference frame $\{C_k\}$ coincides with base frame $\{B_k\}$. Therefore, given the contact arc-length $\sigma_k$, (4) and (5) provide both the unconstrained and constrained kinematics model of the CS. Furthermore, $\theta_{L_k}(t_c)$ and $\delta_k(t_c)$ denote the configurations of the CS at the time of contact $t_c$. $\theta_{L_k}$ and $\delta_k$ denote the commanded configurations of the CS for an instant $t > t_c$.

Constrained differential kinematics is then used to determine the generalized twist of the ED. After collision, contact frame $\{C_k\}$ remains fixed and the forward instantaneous kinematics takes into account the unconstrained portion of the CS. The generalized twist $$t_{g_k/b_k}^{b_k} = \begin{bmatrix} v_{g_k/b_k}^{b_k T} & \omega_{g_k/b_k}^{b_k T} \end{bmatrix}^T$$

of the ED is denoted by a 6×1 vector where $$v_{g_k/b_k}^{b_k} \text{ and } \omega_{g_k/b_k}^{b_k}$$

designate the linear and angular velocities of the ED with respect to base of the CS written in frame $\{B_k\}$. A commanded configuration space vector of an unconstrained segment k is denoted as $\psi_k$. Therefore, by defining $\psi_k = [\theta_{L_k}, \delta_k]^T$ and taking the time derivative of (4), one can relate the linear velocity of the constrained ED with the rate of change of the commanded configuration variables as $$v_{g_k/b_k}^{b_k} = J_{v\psi k} \dot{\psi}_k \qquad (6)$$

The constrained translational Jacobian $J_{v\psi k}$ is given by $$J_{v\psi k} = R_{c_k}^{b_k} \begin{bmatrix} v_1 \cos\delta_k & -v_3 \sin\delta_k \\ -v_1 \sin\delta_k & -v_3 \cos\delta_k \\ v_2 & 0 \end{bmatrix} \qquad (7)$$

where $$v_1 = (L_k - \sigma_k)\frac{1 - \Theta_k \sin\Theta_k - \cos\Theta_k}{\Theta_k^2} \qquad (8)$$

$$v_2 = (L_k - \sigma_k)\frac{\sin\Theta_k - \Theta_k \cos\Theta_k}{\Theta_k^2} \qquad (9)$$

$$v_3 = (L_k - \sigma_k)\frac{1 - \cos\Theta_k}{\Theta_k} \qquad (10)$$

Similarly, the time derivative of (5) and the use of the definition of the angular velocity of the $$ED \, \Omega_{g_k/b_k} \underline{\Delta} [w_{b_k/b_k}^{b_k} \times] = \dot{R}_{g_k}^{b_k} R_{b_k}^{g_k}$$

provide the following differential relation:

$$\omega_{g_k/b_k}^{b_k} = J_{\omega\psi k} \dot{\psi}_k \qquad (11)$$

where the constrained rotational Jacobian $J_{\omega\psi k}$ is given by $$J_{\omega\psi k} = R_{c_k}^{b_k} \begin{bmatrix} -\sin\delta_k & \cos\delta_k \sin\Theta_k \\ -\cos\delta_k & -\sin\delta_k \sin\Theta_k \\ 0 & \cos\Theta_k - 1 \end{bmatrix}. \qquad (12)$$

Equations (7) and (12) are ill-defined when $\theta_{L_k} = \theta_{\sigma_k} = \theta_0$. This singularity is resolved by applying L'Hôpital's rule.

Joint-space differential kinematics defines joint-space variables and relates them to the space variables. Therefore, the joint space variables $q_{k,i} = L_{k,i} - L_k$ are defined in terms of the nominal length of the primary backbone $L_k$, and the lengths of the secondary backbones $L_{k,i}$, $i = 1, \ldots, m$. The configuration space variables $\psi_k$ and the joint space variables $q_k \in \Re^{m \times 1}$ of the $k^{th}$ segment are related as follows:

$$q_k = r(\theta_{L_k} - \theta_0) \begin{bmatrix} \cos\delta_k \\ \vdots \\ \cos(\delta_k + (m-1)\beta) \end{bmatrix} \qquad (13)$$

By taking the time derivative of both sides of (13), the instantaneous inverse kinematics of segment k is given by:

$$\dot{q}_k = J_{q\psi k} \dot{\psi}_k. \qquad (14)$$

Hence, for an n-segment continuum robot the joint-space kinematics is given by:

$$\dot{q} = J_{q\psi} \dot{\psi} \qquad (15)$$

where $$J_{q\psi} = G \begin{bmatrix} J_{q\psi_1} & 0 & \cdots & 0 \\ 0 & J_{q\psi_2} & \ddots & \vdots \\ \vdots & \ddots & J_{q\psi_k} & 0 \\ 0 & \cdots & 0 & J_{q\psi_n} \end{bmatrix}. \qquad (16)$$

$\dot{\psi} \underline{\Delta} [\dot{\psi}_1^T \ldots \dot{\psi}_n^T]^T \in \Re^{2n \times 1}$ is the time derivative of the augmented configuration space vector for a robot with n-independent segments and $\dot{q} \underline{\Delta} [\dot{q}_1^T \ldots \dot{q}_n^T]^T \in \Re^{nm \times 1}$ is the augmented vector of the instantaneous joint velocities. Matrix $G \in \Re^{nm \times nm}$ accounts for actuation coupling among subsequent. For example, if the actuator of the $m^{th}$ backbone in segment $k+1$ is serially attached to the actuator of the $m^{th}$ backbone in segment k then $G = I$. In this case, the actuation unit design is decoupled.

The following mathematical entities that constitute the instantaneous screw of motion of a rigid body are a consequence of Chasles's theorem. The instantaneous motion of a rigid body is fully described by the Plucker line coordinates of the Instantaneous Screw Axis (ISA) and the screw pitch. Thus, the following three entities describe the motion of ED k with respect to local base frame ED, k, with respect to local base frame $\{B_k\}$:

$$r_k = \frac{\omega_{g_k/b_k}^{b_k} \times (v_{g_k/b_k}^{b_k} + p_{g_k}^{b_k} \times \omega_{g_k/b_k}^{b_k})}{\|\omega_{g_k/b_k}^{b_k}\|^2} \quad (17)$$

$$\hat{\omega}_k = \frac{\omega_{g_k/b_k}^{b_k}}{\|\omega_{g_k/b_k}^{b_k}\|} \quad (18)$$

$$\lambda_k = \frac{\hat{\omega}_k^T(v_{g_k/b_k}^{b_k} + p_{g_k}^{b_k} \times \omega_{g_k/b_k}^{b_k})}{\|\omega_{g_k/b_k}^{b_k}\|} \quad (19)$$

Where vector $r_k$ locates the closes point on the screw axis relative to the origin, $\hat{\omega}_k$ is the unit vector along the axis, and $\lambda_k$ is the screw pitch.

In the general case of rigid body motion, (17), (18) and (19) are ill-defined when $$\|\omega_{g_k/b_k}^{b_k}\| = 0.$$

The screw axis lies along the direction of translational velocity and $\lambda_k$=0. However, because of the constrained bending shape of the CS, $$v_{g_k/b_k}^{b_k} \text{ and } \omega_{g_k/b_k}^{b_k}$$

always vanish simultaneously. This means that during motion $\|\omega_{g_k}^{b_k}\|$ is never equal to zero and the special case is excluded.

A better way to compute vector $r_k$ is given by the following least square approximation:

$$r_k = A^\dagger b \quad (20)$$

where superscript † indicates the left pseudo-inverse and $$A = [\Omega_{g_k/b_k}^T \omega_{g_k/b_k}^{b_k T}]^T \quad (21)$$

$$b = [\Omega_{g_k/b_k} p_{g_k}^{b_k} - \Lambda v_{g_k}^{b_k} 0]^T, \quad (22)$$

$$\Lambda = I - \omega_{g_k/b_k}^{b_k} \omega_{g_k/b_k}^{b_k T} / \|\omega_{g_k/b_k}^{b_k}\|^2,$$

and I is the 3×3 identity matrix.

Figure 3:
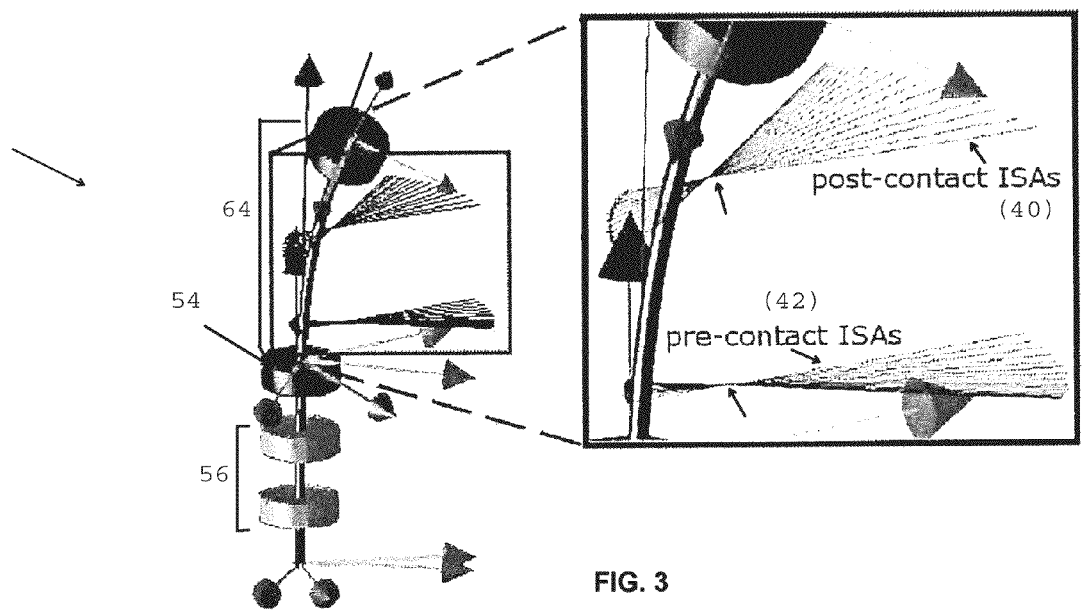
FIG. 3 illustrates the behavior of the instantaneous screw axes (ISAs) of a multi-segment continuum robot before and after a constraint has been applied.

Using (18) and (20) one obtains an axode of motion associated with the motion of the $k^{th}$ ED. Before a collision, a group of ISAs 40 are associated with a first axode of motion. As a consequence of a collision, a second axode of motion, with a second group of associated ISAs 42, is introduced that is the result of a sudden shift as shown in FIG. 3. The figure shows an abrupt gap between pre-contact ISAs 40 and post-contact ISAs 42 when applying the constraint at the third SD 54. The constrained portion 56 of the segment remains fixed while the unconstrained portion 62 bends as a shorter segment with nominal length $L_k - \sigma_k$.

Various approaches can be used to quantify the difference between two infinitesimally separated screws. Since the screw axis is essentially a line, one possible way is to use a Riemannian metric. For spatial motion, the natural generalization of the curve of centrodes is given by the striction curve. An approximation of the striction curve is obtained by concatenating the closest points between infinitesimally separated screw axes. These pairs of points are obtained by the intersection of two consecutive screw axes and their common normal. The striction curve is ill-defined when the CS bends in a fixed plane. In fact, during planar motion, the ISAs are all perpendicular to the bending plane and there are infinite pairs of points that define the minimum distance between the axes. In this case, the striction curve is the curve of centrodes. In order to eliminate this special case and decrease computation effort, a Cartesian metric between the closest points from the origin on the expected ISA based on the kinematics model and on the sensed ISA as obtained from an extrinsic sensor is used.

Although it could be possible to detect a motion discrepancy between the theoretical and actual kinematics by separately monitoring position deviation, orientation deviation, and twist deviation, it would not be possible to find a single, units-consistent metric. The proposed SMD incorporates position, orientation, translational and angular velocities into one entity with units of length.

An extrinsic sensor provides the position $\bar{p}_{g_k}^W$ and orientation $\bar{R}_{g_k}^W$ of the ED of each segment with respect to a world reference frame $\{W\}$. Without loss of generality, $\{W\}$ is aligned with $\{B_1\}$. The relative position and orientation of the kth ED with respect to the previous one is given by $$\bar{p}_{g_k}^{b_k} = \bar{R}_W^{g_{k-1}}(\bar{p}_{g_k}^W - \bar{p}_{g_{k-1}}^W) \quad (23)$$

$$\bar{R}_{g_k}^{g_{k-1}} = \bar{R}_{g_k}^{b_k} = \bar{R}_W^{g_{k-1}} \bar{R}_{g_k}^W. \quad (24)$$

where all entities marked with a bar (i.e., $\bar{p}$) are based on sensor measurements. Equations (23) and (24) provide the decoupled motion of each segment. Using the constrained kinematic model in (4) and (5) with $\sigma_k$=0 (i.e., no contact) the theoretical relative position $p_{g_k}^{b_k}(\sigma_k=0)$ and orientation $R_{g_k}^{b_k}(\sigma_k=0)$ are obtained. The theoretical linear and angular velocities $$v_{g_k/b_k}^{b_k},$$

and $$\omega_{g_k/b_k}^{b_k},$$

are obtained using (6) and (11) respectively. However, the sensed linear and angular velocities $$\bar{v}_{g_k/b_k}^{b_k} \text{ and } \bar{\omega}_{g_k/b_k}^{b_k}$$

are obtained by numerical differentiation of (23) and (24), respectively, along with the definition of angular velocity. These theoretical and sensed relative positions and velocities are used to define the following Screw Motion Deviation (SMD):

$$\mu_k = \|r_k(\sigma_k=0) - \bar{r}_k\| \quad (25)$$

where $\bar{r}_k$ is calculated using (17).

The use of relative motion data for $\mu_k$ decouples the SMDs and provides the basis for collision detection and estimation of contact location along any segment of the continuum robot independently.

The following methods for collision detection and contact estimation location are based on the principles set forth above.

Ideally, for a perfect robot, a perfect controller, and a perfect sensor, one would obtain $\mu_k=0$. However, because of uncertainties due to kinematic model approximations, an uncalibrated robot, extension of the actuation lines, and sensor noise, $\mu_k$ will be bounded by a certain distance threshold $\epsilon_k$ during unconstrained motion. Collision is therefore independently detected for any segment when $\mu_k > \epsilon_k$ for k=1, 2, ..., n.

In the case of electromagnetic tracking devices, threshold $\epsilon_k$ is time, position, and velocity dependent because the accuracy varies depending on the workspace and the proximity to ferromagnetic and conductive metals. Although it is possible to improve the accuracy of these devices by recalibrating the device, it can be assumed that non-static ferromagnetic objects are present in the proximity of the robot. Furthermore, if a low-order difference method is used for differentiating (23) and (24) with respect to time, low velocities amplify the noise components and increase the variance of the SMD. For this reason the algorithm needs to filter out false positive due to noise ratio when $$\|\omega_{g_k/b_k}^{b_k}\| < \zeta_k$$

where $\zeta_k$ is a threshold with units of rad/s.

Figure 4:
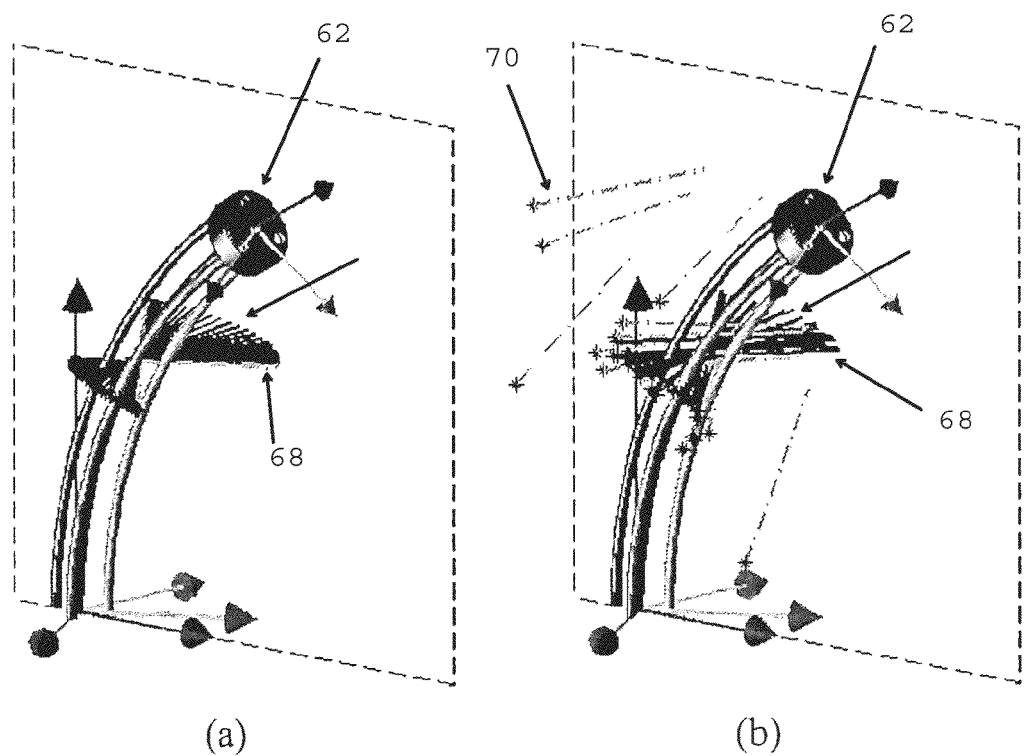
FIG. 4 illustrates the effect of pose measurement noise on a locus of an ISA of a multi-segment continuum robot.

This phenomenon is shown in FIG. 4. FIG. 4a shows an unconstrained CS 62 following a quintic polynomial trajectory in configuration space. The axode of motion, i.e., the group of infinitesimally separated ISAs 68 lies compact. The dashed ISAs 68 are associated with $$\|\omega_{g_k/b_k}^{b_k}\| < \zeta_k.$$

Since the motion is generated with a quintic polynomial, the dashed ISAs 68 are associated with the beginning and the end of the motion. FIG. 4b shows the CS 62 following the same trajectory but the position and twist of its ED are perturbed with white Gaussian noise 70. When the magnitude of the noise is comparable to the magnitude of the linear and angular velocities, the screw of motion obtained with (18) and (20) loses any physical significance.

If the sensor samples at frequency $f_s$ [Hz] with resolution $\epsilon$ [rad], then the value of $\zeta_k$ must meet the following constraint for trustworthy velocity measurements:

$$\zeta_k > \alpha \epsilon_s f_s \qquad (26)$$

where $\alpha > 1$ (ideally 2 or 3). Threshold $\zeta_k$ is proportional to sensor resolution $\epsilon$ and sample frequency $f_s$ and defines the lowest angular velocity of each end disk under which no contact can be detected. There are two ways to reduce the critical angular velocity magnitude $\zeta_k$: increase sensor resolution or decrease sampling frequency. Although the latter solution also decreases threshold $\zeta_k$, it also degrades the responsiveness of the collision detection algorithm by introducing lag into the system. However, since the minimal and maximal allowable twist is generally known once a task is defined, threshold $\zeta_k$ can be tuned accordingly.

Thus, the following binary function is defined:

$$\mathcal{F}(t) = \begin{cases} 1 & \mu_k > \epsilon_k \\ 0 & \mu_k \leq \epsilon_k \end{cases} \qquad (27)$$

Once $\mu_k > \epsilon_k$ and $$\|\omega_{g_k/b_k}^{b_k}\| < \zeta_k,$$

collision is detected when $$\sum_{t=t_c}^{t_c+Q\Delta_t} \mathcal{F}(t) = Q \qquad (28)$$

where $t_c$ is the first instant which is $\mu_k > \epsilon_k$, $\Delta_t$ is time step constant, and Q is the width of the collision detection window that allows to filter out false positives.

Figure 5:
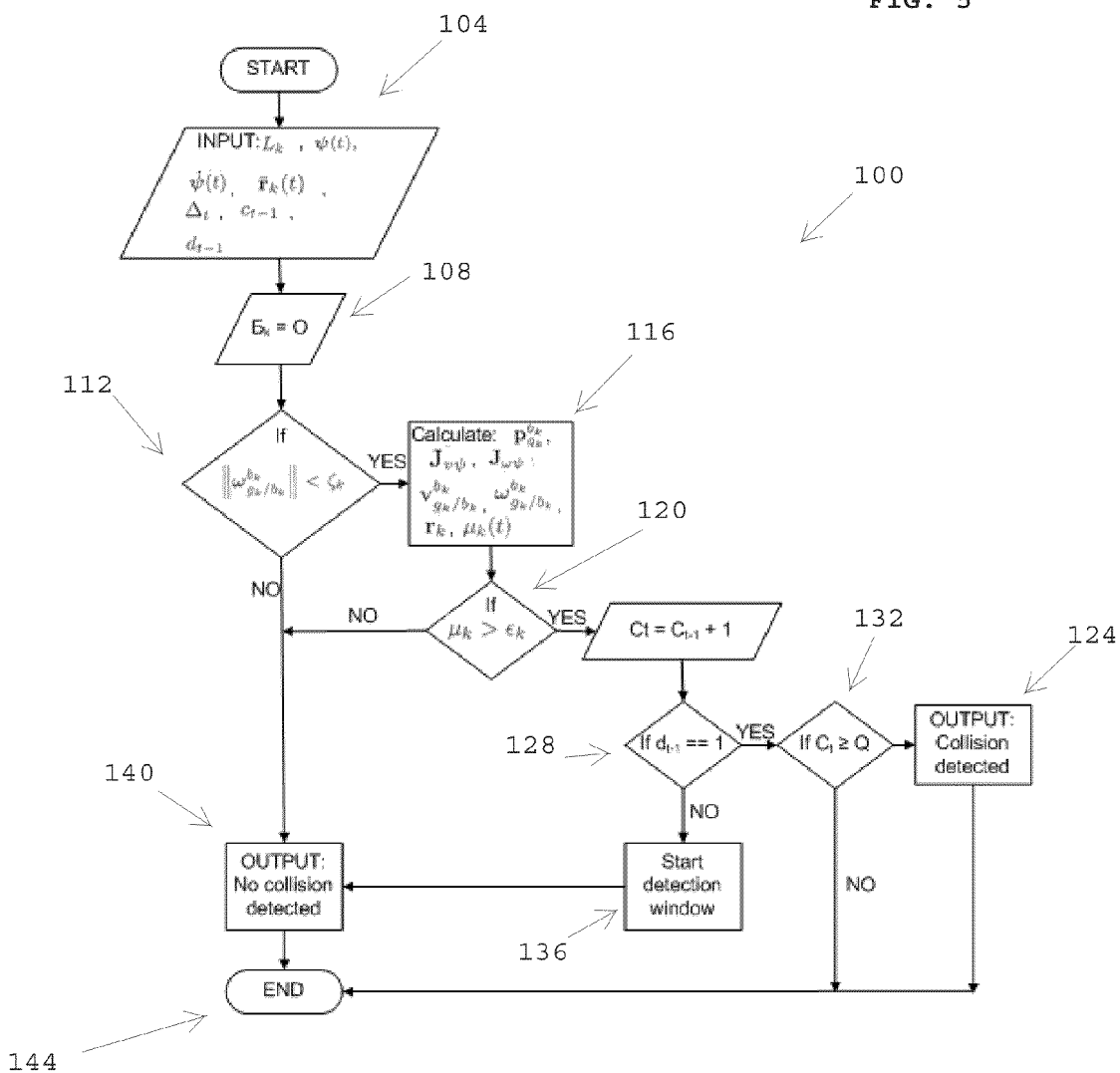
FIG. 5 is a flowchart that demonstrates a method for contact detection along a multi-segment continuum robot according to one embodiment of the invention.

FIG. 5 is a flow chart illustrating a collision detection strategy or method (i.e., algorithm) 100 according to one embodiment of the invention. FIG. 5 includes the process that determines when a portion of a robot contacts an object, e.g., a wall of a cavity. The following parameters are introduced, as is indicated at 104, as initial inputs: the nominal length of the segment, $L_k$, the closest point from the origin on the sensed ISA, $\bar{r}_k(t)$, the commanded configuration space orientation, $\psi(t)$, its time derivative $\dot{\psi}(t)$, a counter variable $c_{t-1}$, a binary variable $d_{t-1}$, and the time step $\Delta_t$. The method also initializes the contact arc-length $\sigma_k=0$, at 108, so that the unconstrained model of the CS is used. Thus, the method checks if the magnitude of the angular velocity is high enough to have meaningful sensor data 112. If this condition is met, the motion residual is calculated using equations (4), (7), (12), (6), (11), and (20), which is indicated at 116. Next, the method checks at 120 whether $\mu_k > \epsilon_k$. In the case of detection 124, the method checks if the collision detection window was previously started 128. If so, the counter variable $c_{t-1}$ is incremented and used for future iterations. When the condition in (27) is met 132, collision is detected. If the method determines that the window has not been previously started 128, the detection window is started 136. If the magnitude of the angular velocity is not high enough to have meaningful sensor data 112 or that $\mu_k \leq \epsilon_k$ 120, then no collision is detected 140. The method includes two outputs, each of which prompts the end of the method 144.

For an n-segment continuum robot, the collision detection method described above identifies which segments are constrained by the environment. Therefore, an auxiliary strategy or method (i.e., algorithm) narrows down the estimation of contact location at the segment level. Immediately after collision, a constrained single segment behaves as described in according to kinematic theory, explained above. Multiple segments behave according to this theory as well if the stiffness of two subsequent segments is comparable. The stiffness of constrained segment k+1 needs to be high enough to prevent the motion of segments k=1, ..., k.

Figure 6:
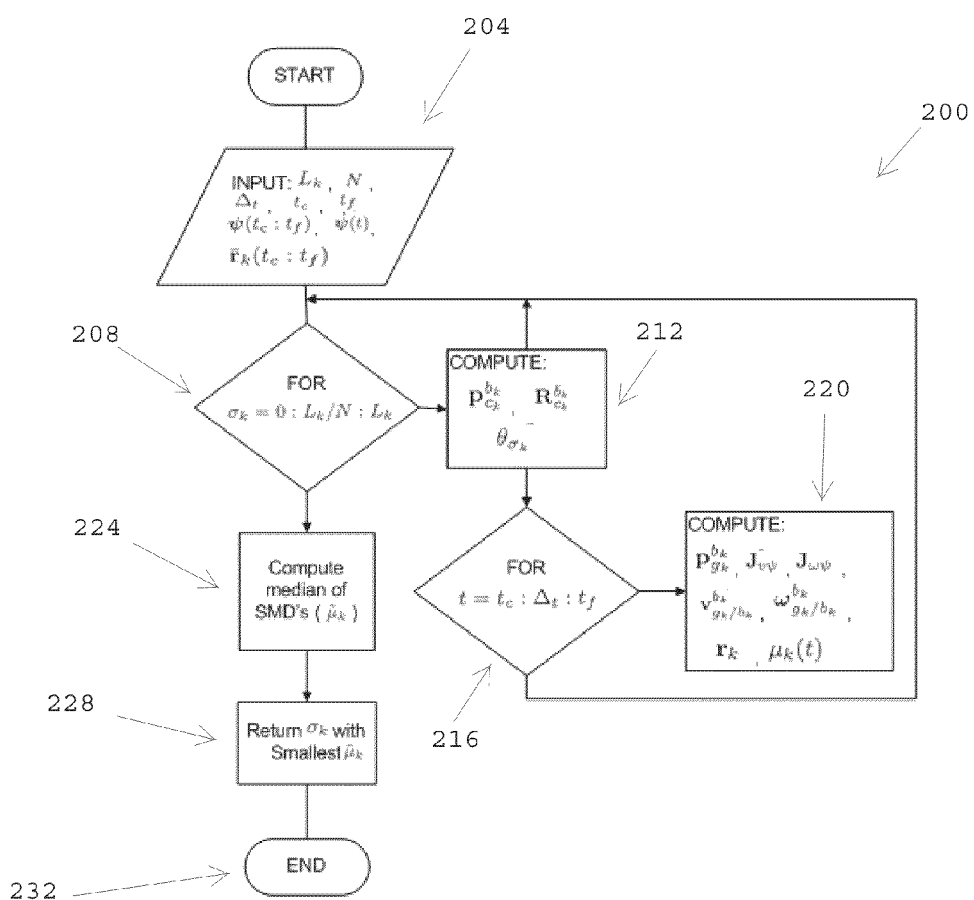
FIG. 6 is a flowchart that demonstrates a method for contact location estimation at the segment level along a multi-segment continuum robot according to one embodiment of the invention.

FIG. 6 is a flow chart of a method of estimating contact location 200 according to an embodiment of the present invention. A preliminary step 204 to the estimation method is to input the following parameters. Input N is the parameter that defines the level of discretization for the estimation. In the case of the continuum robot shown in FIG. 7 the contact is most likely to occur at any of the SDs that are placed $L_k/N$ apart from each other. Another input is $\Delta_t$ the time step associated with the extrinsic sensor. Additional inputs are $t_c$ and $t_f$, the first and last instants of the detection window initiated by the contact detection method 100. Further inputs include $\psi(t_c:t_f)$ and $\bar{r}_k(t_c:t_f)$, the desired configuration space trajectory and the time history of closest point on the sensed ISA, respectively. Once the method is initialized, the method collects the SMDs by way of computing equations (1), (2), and (3), at 212, associated with each guessed $\sigma_k$ 208 and finds the arithmetic mean of the SMD 224 for instants of time included into the detection window 216, by way of equations (4), (7), (12), (6), (11), and (20), at 220. The method finally returns the contact arc-length $\sigma_k$ associated with the smallest SMD 228 to complete the location estimation process 232.

Figure 7:
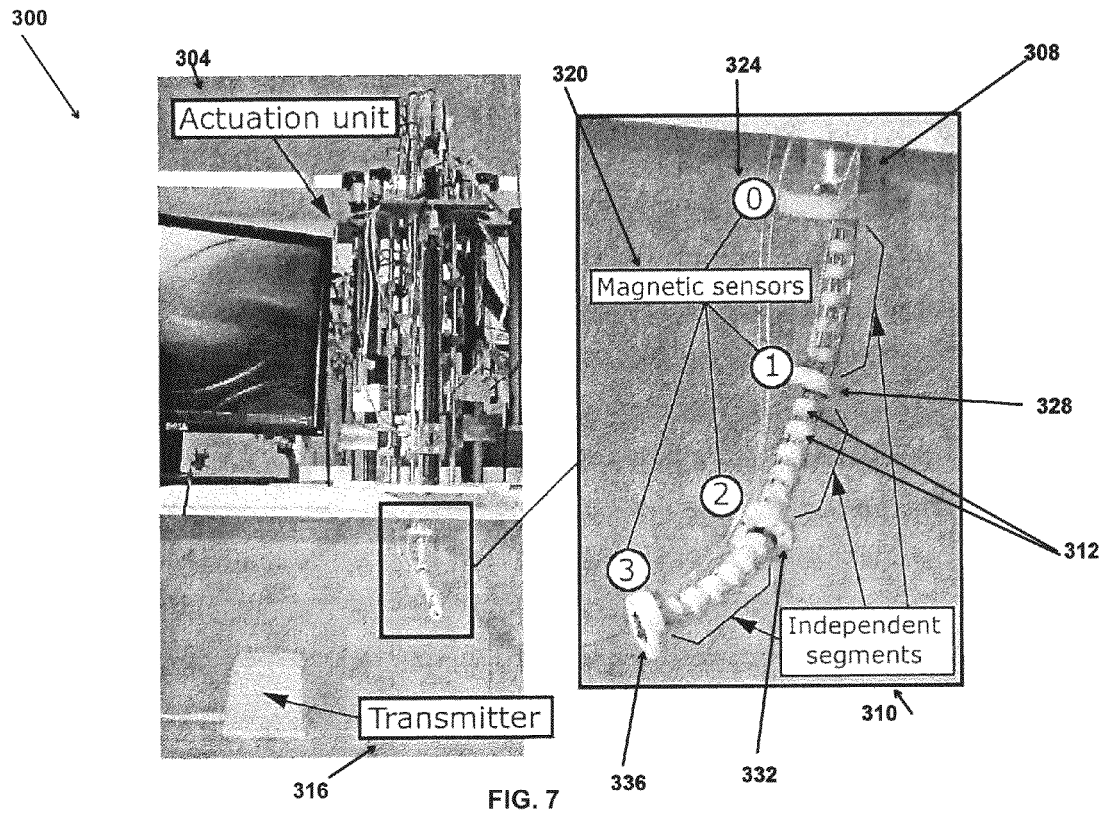
FIG. 7 is an example of a system capable of implementing the methods for contact detection and contact location estimation.

The accuracy of the estimation of contact location method not only depends on the kinematic modeling arguments described above but it is also affected by the discretization parameter N. Small values of discretization parameter N are associated with finer minimization problems. For the robot 308 as is shown in FIG. 7, N is equal to the number of SDs 312. This means that the method identifies the disk at which the contact is most likely to occur. Contacts in between two adjacent SDs are associated with one of the two disks.

With further reference to FIG. 7, the robot 308 illustrates one example of a part of a system 300 equipped to implement the methods for contact detection and location estimation as described above and in FIGS. 5-6. The system 300 illustrated in FIG. 7 includes a 6-degree-of-freedom (6 DOF) 3-segment multi-backbone continuum robot 308 according to the specifications reported in Table II below, an actuation unit 304, and an electromagnetic tracker 316 (e.g., an Ascension 3D Guidance trakSTAR®). The electromagnetic tracker 316 has an RMS accuracy of 1.4 mm in position and 0.50 in orientation. The robot 308 is equipped with four sensors 320 (e.g., 6 DOF Model 130) positioned at the robot's base 324, first segment ED 328, second segment ED 332, and end-effector 336, respectively. The placement of sensors 324, 328, 332, 336 delineates the segments 310 each made of spacer disks 312.

TABLE II

ROBOT'S SPECIFICATIONS AND COLLISION THRESHOLDS

| | segment 1 | segment 2 | segment 3 |
|---|---|---|---|
| L [mm] | 50 | 50 | 45 |
| disk height [mm] | 3.5 | 3.5 | 3.5 |
| spacing [mm] | 3.6 | 3.6 | 3.4 |
| # of disks | 7 | 7 | 6 |
| $\epsilon_k$ [mm] | 10 | 8 | 8 |
| $\zeta_k$ [rad/s] | 0.1 | 0.1 | 0.1 |

Figure 8:
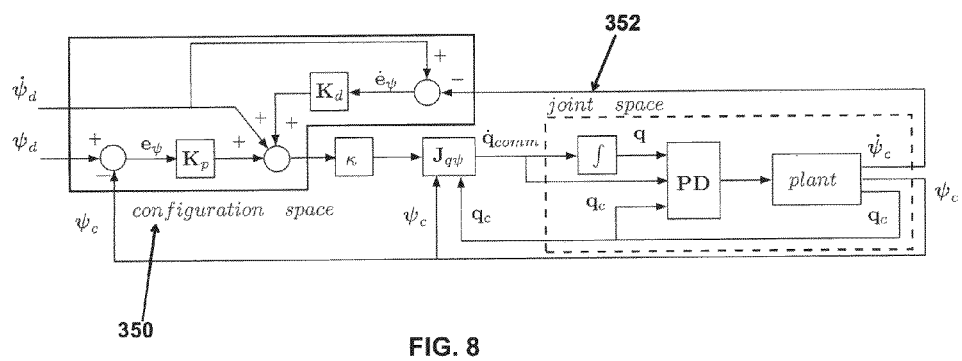
FIG. 8 is a block diagram of the proposed tiered mixed feedback controller for a multi-segment continuum robot.

The continuum robot 308 is controlled with a mixed configuration- and joint-space feedback architecture, indicated at 350 and 352 in FIG. 8. The configuration space feedback is provided by the same sensor used in the collision detection and estimation of contact location algorithms. This additional feedback reduces the configuration space tracking error but does not affect the task space tracking error. This discrepancy is the basis of the method presented above.

A configuration space error $e_\psi$ is introduced below as a deviation of the current configuration space vector $\psi_c$ from the desired configuration space vector $\psi_d$ $$e_\psi = \psi_d - \psi_c \quad (29)$$

The time derivative of (29) when accounting for (16) and the compensation factor K>1 yields:

$$\dot{e}_\psi = \dot{\psi}_d - \eta \kappa J_{q\psi}^\dagger \dot{q}_{comm} \quad (30)$$

where superscript † denotes the pseudo-inverse, $\dot{q}_{comm}$ is the commanded augmented vector of joint speeds, and $\eta$ is a positive scalar corresponding to sensor and plant uncertainties. The control input to the low-level joint-space controller is given by:

$$\dot{q}_{comm} = \kappa J_{q\psi}(\dot{\psi}_d + K_p e_\psi + K_d \dot{e}_\psi). \quad (31)$$

The following discussion presents examples of single-contact collision detection, multi-contact collision detection, collision detection repeatability, and estimation of contact location. The robot 308 illustrated in FIG. 7 is commanded from starting configuration $\psi_s = [72° \ 0° \ 72° \ 0° \ 72° \ 45° \ 1]$ to final configuration $\psi_f = [45° \ 45° \ 45° \ -450 \ 45° \ 45°]$ using a quintic polynomial trajectory in configuration space with accomplishment time of five seconds.

Single-Contact Collision Detection

Figure 9:
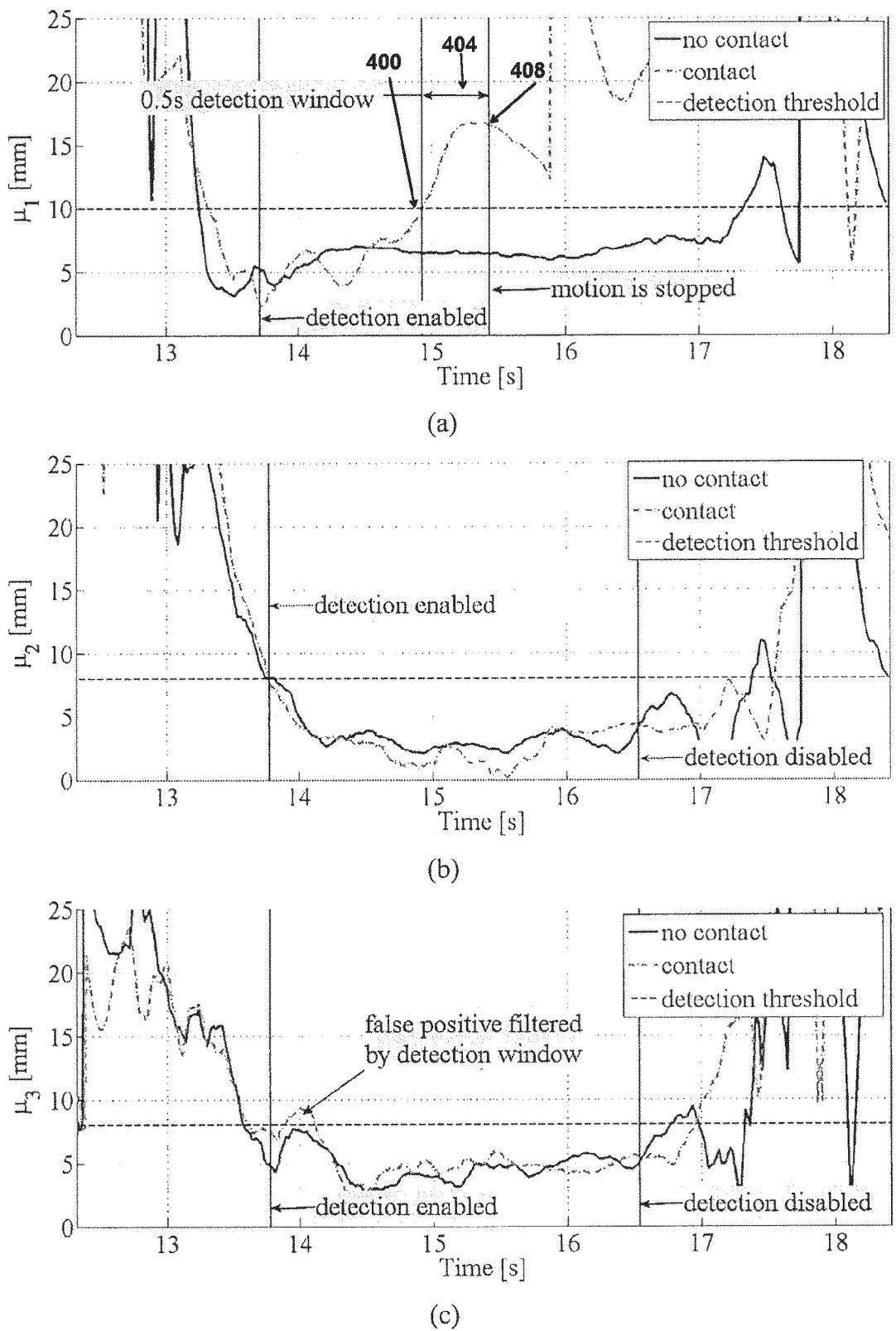
FIGS. 9a-9c graphically illustrate time histories $\mu_1$, $\mu_2$, and $\mu_3$, respectively, when a constraint acts at a first segment of a multi-segment continuum robot.
Figure 10:
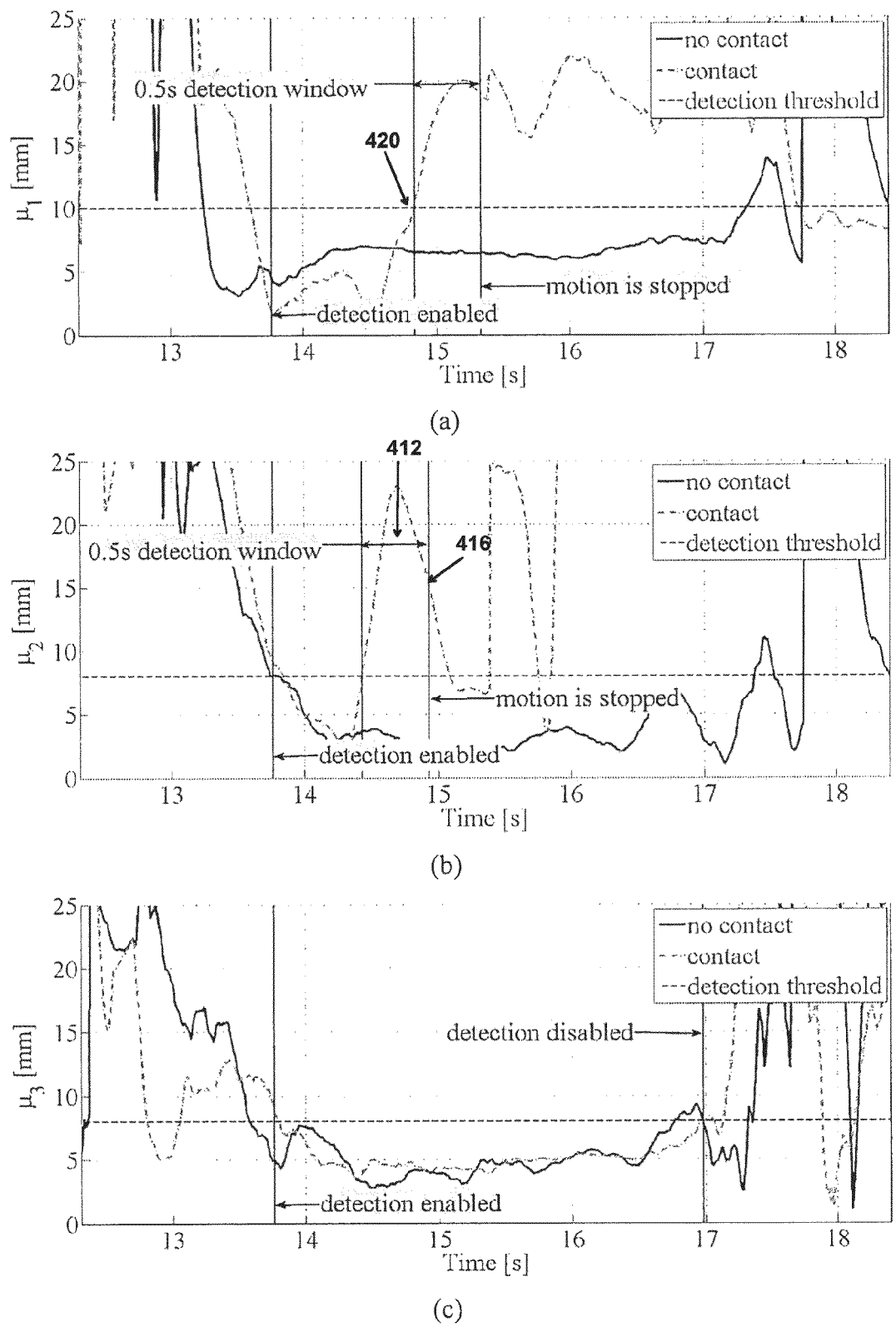
FIGS. 10a-10c graphically illustrate time histories $\mu_1$, $\mu_2$, and $\mu_3$, respectively, when a constraint acts at a second segment of a multi-segment continuum robot.
Figure 11:
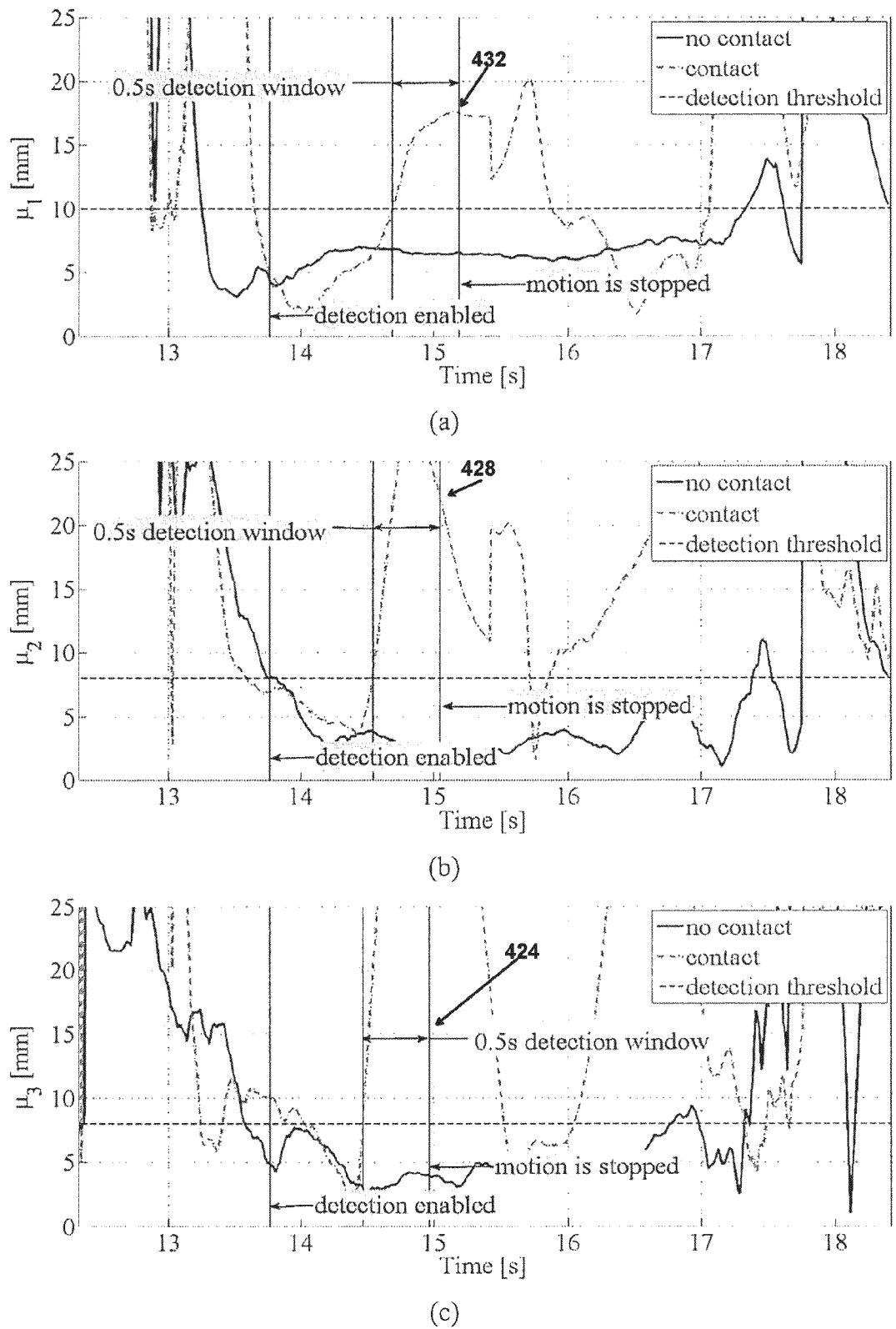
FIGS. 11a-11c graphically illustrate time histories $\mu_1$, $\mu_2$, and $\mu_3$, respectively, when a constraint acts at the third segment of a multi-segment continuum robot.

FIGS. 9-11 include a first set of graphs that demonstrate the ability of the collision detection algorithm to detect a single collision acting along the continuum robot 308. The vertical lines labeled "detection enabled" and "detection disabled" designate the portion of the trajectory with the angular velocities magnitudes bigger than 0.1 rad/s as described in the contact detection method described above.

In a first example, the first segment of the continuum robot 308 is constrained during the motion. The time histories of SMDs $\mu_1$, $\mu_2$, and $\mu_3$ are presented in FIG. 9. The SMD of the first segment (FIG. 9a) rises above the threshold at approximately t=15 s, indicated at 400. After a detection window 404 of a half second, collision is successfully triggered, indicated at 408. The SMDs associated with the second and third segments (FIGS. 9b and 9c respectively) are not affected by the constraint.

In a second example, the second segment of the continuum robot 308 is constrained during the motion. The time histories of SMDs $\mu_1$, $\mu_2$, and $\mu_3$ are presented in FIG. 10. Collision is detected 416 at the second segment (FIG. 10b) at approximately t=14.9 s after a collision window of a half second, indicated at 412. The SMD $\mu_1$ associated with the first segment is also affected by the contact and rises above the threshold at approximately t=14.8 s, indicated at 420. The difference in contact times indicates a delay that is due to the compliance of the segments and distinguishes between single and multiple collisions. Also in this case, the SMD $\mu_3$ associated with the third segment remains unaffected.

In a third example, the third segment of the continuum robot 308 is constrained during the motion. The time histories of SMDs $\mu_1$, $\mu_2$, and $\mu_3$ are presented in FIG. 11. Collision is detected, indicated at 424, at third segment at t=14.953 (FIG. 11c). Similar to the second example above, the two proximal segments are also affected by the contact as shown by their respective SMDs (FIGS. 11a and 11b) 428, 432.

The methods for contact detection and contact location estimation provide the ability to successfully detect collisions with a soft constraint and other continuum arms. This capability is of primary importance when the method is implemented on surgical continuum robots and surgical robotic systems with continuum end-effectors. The collision detection method is able to prevent inadvertent trauma to delicate surrounding tissues by triggering a reaction strategy.

Multi-Contact Collision Detection

Figure 12:
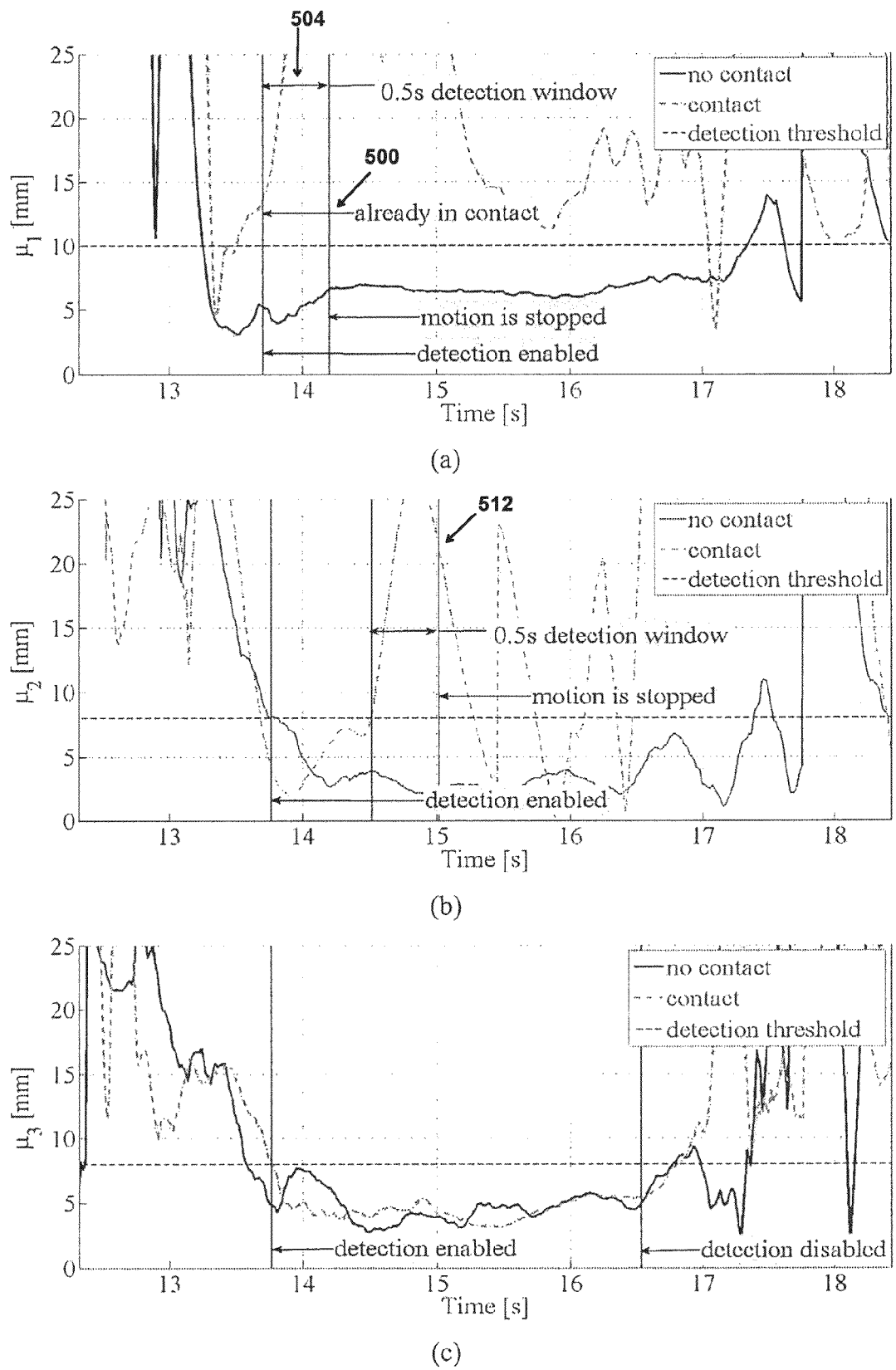
FIGS. 12a-12c graphically illustrate time histories $\mu_1$, $\mu_2$, and $\mu_3$, respectively, when a constraint acts at multiple segments of a multi-segment continuum robot.

With reference to FIG. 12, a second set of graphs demonstrates the ability of the collision detection algorithm to detect multiple collisions. The constraints act on different segments of the robot 308 and, in the case of a two-contact collision, the proximal segment collides first. This is possible by using one of the following reaction strategies: once the collision is detected, the motion of the constrained segments is stopped while the unconstrained segments continue the pre-assigned trajectory. FIG. 12 shows the time histories of the SMDs $\mu_1$, $\mu_2$, and $\mu_3$. Collision with the first segment is detected at approximately t=14.28 s (FIG. 12a), indicated at 500. The detection window 504 is initiated immediately after the collision detection is enabled 508. Collision at the second segment is detected at approximately t=15 s (FIG. 12b), indicated at 512. The main difference between FIG. 12 and FIG. 10 is the order in which collisions are detected. In FIG. 10 collision is first detected at the second segment and then at the first segment. On the other hand, in FIG. 12 collision is first detected at the first segment and then at the second segment. The order in which the collisions are detected allows for discerning between a single contact acting at the second segment and multiple contacts acting at the first and second segment. Similar to the previous case studies, the SMD associated with the third segment is not affected and no collision is detected (FIG. 12c).

Repeatability of Collision Detection

Figure 13:
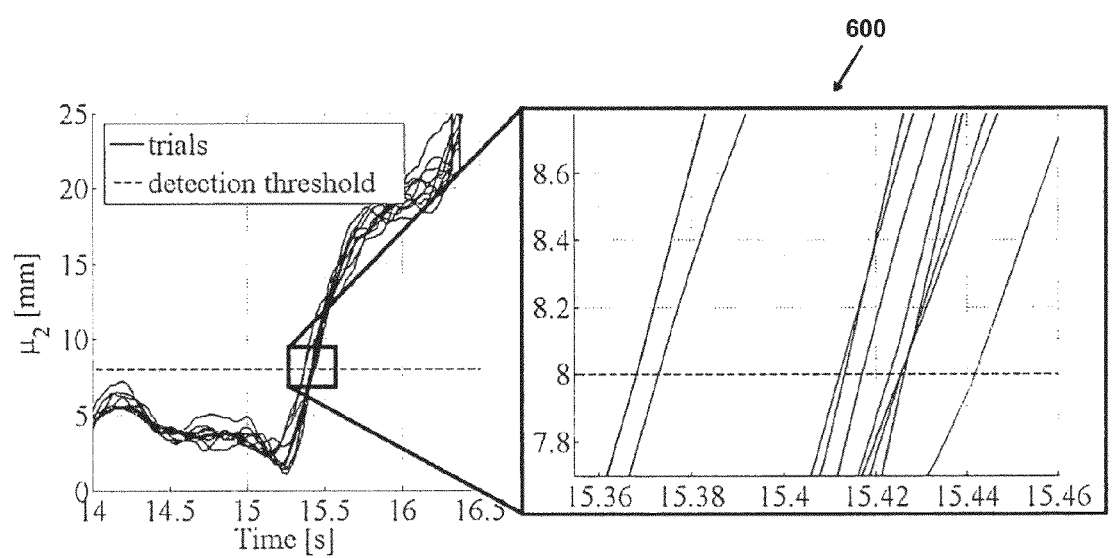
FIG. 13 illustrates a repeatability analysis for contact detection for time history $\mu_2$.

The repeatability of the collision detection algorithm is quantified in FIG. 13. As an example, the second segment of the continuum robot 308 impacts a static, rigid object ten times. The constraining object is a carbon fiber tube covered with silicon material to increase friction at the contact point and reduce slippage. The time history of the SMD $\mu_2$ for all ten trials is shown in FIG. 13. The instant of collision 600 varies by only 0.07 s demonstrating a very high repeatability.

Estimation of Contact Location

The performance of the estimation method is reported in FIGS. 14-16. Each experiment was repeated five times and the obstacle was adjusted to constrain one of the SDs of the continuum robot 308. However, because of the small size of the robot, the contact can occur at any location along the disk's width.

With reference to FIGS. 14-16, column $d_i$, indicates which disk was impacted and column T indicates the experiment trial number. The remaining eight columns $d_0, \ldots, d_7$ report the arithmetic average of the SMD associated with each guessed constrained disk location as described in the method for contact estimation (FIG. 6). In particular, $d_0$ represents the BD (i.e., no contact) and $d_7$ represents the ED (i.e., segment completely constrained). In each row, the entry associated with the smallest SMD is highlighted in gray.

The estimation of contact location on the proximal segment of the continuum robot 308 is presented in FIG. 14. Very small SMDs for two consecutive disks (3.64 mm apart from each other) was noted. This discrepancy in estimating the location of contact corresponded to a worst-case scenario error of at most the height of two SDs and the space between two adjacent disks (see FIG. 14). The sources of uncertainty and the possible slippage of the robot with respect to the rod indicated that the error in estimating the contact location within one disk error was anticipated. While a finer discretization of the guessed location in the contact estimation method (FIG. 6) would result in smaller errors a simple training/calibration technique would certainly lead to exact identification of the constrained disk.

The estimation of contact location on the second segment of the continuum robot 308 is presented in FIG. 15. The success rate of the algorithm was appreciably higher than the previous case study. The improvement was due to better noise/signal ratio and a smaller collision threshold as shown in FIGS. 10a and 10b. The third disk was successfully identified four times out of five and the fourth disk was successfully identified five times out of five. In the case of the second and fifth disks, the algorithm indicated a very small deviation between consecutive disks 1, 2 and 5, 6.

The estimation of contact location on the third segment of the continuum robot 308 is presented in FIG. 16. The performance of the estimation algorithm appeared to be more problematic because the constrained portion of a constrained segment did not remain fixed while the free portion bent like a shorter segment. The lower stiffness of the third CS resulted in dramatic deformation of the segment invalidating the constrained differential kinematics model presented above.

The collision detection algorithm presented offers immediate application for safeguarding against inadvertent anatomical trauma in robotic systems equipped with multiple continuum arms. This algorithm is even effective when the robot contacts soft and non-static objects like human fingers and other continuum arms. There are consistent margins for decreasing the detection thresholds after proper calibration of the magnetic tracker device and kinematics parameters of the robot. Despite this, the adoption of the motion deviation described already allows for robust collision detection. The proposed motion deviation incorporates the position, the orientation, and the twist of each actuated segment into a single entity thereby preserving unit consistency.

The estimation of contact location is shown to be effective in the case in which the stiffness of all the individually actuated segments is comparable. Furthermore, screw theory not only allows for estimating the contact location, as demonstrated, but will also provide constraint acting on the continuum segment.

Thus, the invention provides, among other things, a unified framework for collision detection and localization of contacts along continuum robots. Various features and advantages of the invention are set forth in the following claims.

What is claimed is:

1. A method for collision detection along a continuum robot, the method comprising:
   inserting a portion of the continuum robot into a cavity or operating the continuum robot among obstacles, the continuum robot including a plurality of independent segments;
   detecting contact between the robot and a wall of the cavity or surrounding obstacles;
   determining in which one of the segments of the robot the contact occurred; and
   moving the robot such that the segment determined to be in contact with the wall of the cavity moves laterally out of contact with the wall of the cavity in real-time after contact with the wall of the cavity is detected without retracting the continuum robot from the cavity.

2. The method of claim 1 further comprising determining whether contact between the robot and the wall of the cavity occurred in more than one segment of the continuum robot.

3. method of claim 2 wherein, if contact between the robot and the wall of the cavity occurred in more than one segment, determining a first segment and a second segment where the contact occurred.

4. The method of claim 1 further comprising stopping movement of the robot when contact is detected.

5. A method for generating a constraint, the method comprising:
   inserting a continuum robot into a cavity, the continuum robot including a plurality of independent segments;
   detecting contact between the robot and a wall of the cavity and generating a contact data identifier;
   determining in which one of the segments of the robot the contact occurred and generating a location data identifier;
   generating a constraint based on the contact data identifier and the location data identifier;

moving the continuum robot such that the segment determined to be in contact with the wall of the cavity moves laterally out of contact with the wall of the cavity in real-time after contact with the wall of the cavity is detected without retracting the continuum robot;

removing the robot from the cavity; and inserting a tool into the cavity based on the constraint.

6. The method of claim 5 further comprising detecting whether additional contacts occurred between the robot and the wall of the cavity, and thereby generating additional contact data identifiers.

7. The method of claim 6 further comprising detecting in which ones of the segments the additional contacts occurred, and thereby generating additional location data identifiers.

8. The method of claim 7 further comprising generating a plurality of constraints based on the additional contact data identifiers and the additional location data identifiers.

9. The method of claim 8 further comprising generating a map of the cavity based on the plurality of constraints.

10. A robotic system comprising:
a continuum robot having a plurality of independent segments; and
a controller in communication with the robot, the controller including a processor and a software program stored in a non-transitory computer readable medium accessible by the computer processor, the software program being operable to
determine whether the robot contacts a structure,
if contact occurred, determine in which one of the segments of the robot the contact occurred, and
automatically move the robot such that the segment determined to be in contact with the structure moves laterally out of contact with the structure without retracting the continuum robot from the cavity.

11. The robotic system of claim 10 wherein the software program is further operable to teach the robot controller to construct a virtual fixture.

12. The robotic system of claim 11 wherein the virtual fixture prevents portions of the robot from impinging against obstacles.

13. The robotic system of claim 10 wherein the software program is further operable to filter commands if contact occurs such that additional contact is prevented.

14. The robotic system of claim 12 wherein the commands protect at least two arms of the robot from impingement during telemanipulation.

15. The robotic system of claim 10 wherein the software program is further operable to explore a non-visible cavity such that the robot responds to contact.

16. The robotic system of claim 14 wherein contact provides the robot with cues for further exploration of the cavity.

17. The robotic system of claim 15 wherein the cues are used to generate a map of the cavity.

18. The method of claim 1, further comprising controlling movement and pose of the continuum robot using an external actuator,
wherein detecting contact between the robot and a wall of the cavity includes detecting when movement of the continuum robot is constrained by an external force, and
wherein determining in which one of the segments of the robot the contact occurred includes determining which specific independently controlled segment of the continuum robot has its movement constrained by the external force.

* * * * *